United States Patent
Gewehr et al.

(10) Patent No.: US 7,501,530 B2
(45) Date of Patent: Mar. 10, 2009

(54) TRIFLUOROMETHYL-THIOPHENE CARBOXYLIC ACID ANILEDES AND USE THEREOF AS FUNGICIDES

(75) Inventors: Markus Gewehr, Kastellaun (DE); Bernd Müller, Frankenthal (DE); Thomas Grote, Wachenheim (DE); Wassilios Grammenos, Ludwigshafen (DE); Andreas Gypser, Mannheim (DE); Jordi Tormo i Blasco, Laudenbach (DE); Anja Schwögler, Mannheim (DE); Joachim Rheinheimer, Ludwigshafen (DE); Carsten Blettner, Mannheim (DE); Frank Schieweck, Heβheim (DE); Michael Rack, Heidelberg (DE); Ulrich Schöfl, Brühl (DE); Siegfried Strathmann, Limburgerhof (DE); Reinhard Stierl, Freinsheim (DE); Jan Rether, Kaiserslautern (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 331 days.

(21) Appl. No.: 10/548,840

(22) PCT Filed: Mar. 20, 2004

(86) PCT No.: PCT/EP2004/002933

§ 371 (c)(1),
(2), (4) Date: Sep. 12, 2005

(87) PCT Pub. No.: WO2004/085419

PCT Pub. Date: Oct. 7, 2004

(65) Prior Publication Data

US 2006/0172891 A1    Aug. 3, 2006

(30) Foreign Application Priority Data

Mar. 24, 2003  (DE) ............... 103 13 126
Nov. 21, 2003  (DE) ............... 103 54 549

(51) Int. Cl.
*C07D 333/22* (2006.01)
*C07C 333/32* (2006.01)
*A01N 25/00* (2006.01)
*C07C 335/00* (2006.01)
*A01N 25/32* (2006.01)

(52) U.S. Cl. ............... 549/72; 549/64; 424/405
(58) Field of Classification Search ............... 549/64, 549/72; 424/405
See application file for complete search history.

(56) References Cited

U.S. PATENT DOCUMENTS

| | | |
|---|---|---|
| 6,319,940 B1 | 11/2001 | Elbe et al. |
| 6,534,532 B1 | 3/2003 | Elbe et al. |
| 2003/0078287 A1 | 4/2003 | Elbe et la. |
| 2004/0039043 A1 | 2/2004 | Elbe et al. |

FOREIGN PATENT DOCUMENTS

| | | |
|---|---|---|
| EP | 0 915 868 A | 3/1999 |
| JP | 62-249966 A | 10/1987 |
| JP | 62-249975 A | 10/1987 |
| JP | 1-313402 A | 12/1989 |
| WO | WO-02/08197 A1 | 1/2002 |

OTHER PUBLICATIONS

Derwent Publication Ltd., 87-345557/49, Apr. 22, 1986.
Derwent Publication Ltd., 87-345550/49, Apr. 22, 1986.
Derwent Publication Ltd., 90-034367/05, Jun. 13, 1988.

*Primary Examiner*—Johann R Richter
*Assistant Examiner*—Andriae M Holt
(74) *Attorney, Agent, or Firm*—Birch, Stewart, Kolasch & Birch, LLP

(57) ABSTRACT

The invention relates to novel biphenyl carboxamides of formula (I), wherein A, R, Z, X, Y, m and n have the meanings given in the description, to multiple methods for producing these substances, to their use for combating unwanted microorganisms and to novel intermediate products and the production thereof.

13 Claims, No Drawings

TRIFLUOROMETHYL-THIOPHENE CARBOXYLIC ACID ANILEDES AND USE THEREOF AS FUNGICIDES

The present invention relates to trifluoromethylthiophenecarboxanilides of the general formulae I, II and III

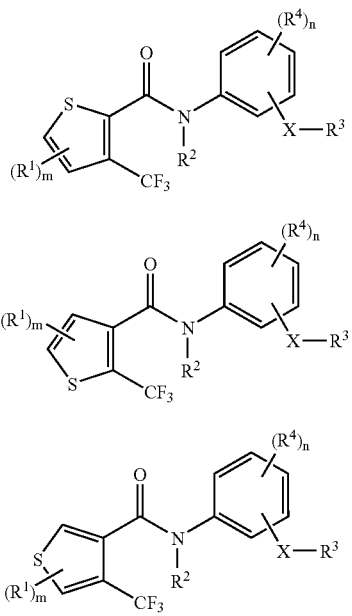

in which the substituents are as defined below:

$R^1$, $R^4$ independently of one another are $C_1$-$C_4$-alkyl, $C_3$-$C_6$-cycloalkyl, $C_2$-$C_4$-alkenyl, $C_2$-$C_4$-alkynyl, $C_1$-$C_4$-alkoxy (it being possible for these groups to be substituted by halogen), H, halogen, nitro, CN;

$R^2$ is H, OH, $C_1$-$C_4$-alkyl, $C_3$-$C_6$-cycloalkyl, $C_1$-$C_4$-alkoxy (it being possible for these groups to be substituted by halogen);

$R^3$ is $C_1$-$C_{12}$-alkyl, $C_3$-$C_{12}$-cycloalkyl, $C_2$-$C_{12}$-alkenyl, $C_5$-$C_{12}$-cycloalkenyl, $C_2$-$C_{12}$-alkynyl, $C_3$-$C_{12}$-cycloalkyl-$C_1$-$C_4$-alkyl (it being possible for these groups to be substituted by $R^7$); phenyl, phenyl-$C_1$-$C_6$-alkyl, phenyl-$C_2$-$C_6$-alkenyl, phenyl-$C_2$-$C_6$-alkynyl, phenyloxy-$C_1$-$C_6$-alkyl, phenyloxy-$C_2$-$C_6$-alkenyl, phenyloxy-$C_2$-$C_6$-alkynyl, where the alkyl, alkenyl and alkynyl moiety may be substituted by $R^7$ and the phenyl ring may be substituted by $R^5$; —C($R^8$)=NOR$^6$;

X is O, S or a direct bond;

$R^5$ is H, $C_1$-$C_4$-alkyl, $C_3$-$C_6$-cycloalkyl, $C_1$-$C_4$-alkoxy, $C_2$-$C_4$-alkenyl, $C_2$-$C_4$-alkynyl (it being possible for these groups to be substituted by halogen), halogen, nitro, CN, phenyl (which may be substituted by $R^1$), phenoxy (which may be substituted by $R^1$), $C_1$-$C_6$-alkylphenyl, where the alkyl moiety may be substituted by halogen and the phenyl ring may be substituted by $R^1$;

$R^6$ is $C_1$-$C_4$-alkyl, $C_3$-$C_6$-cycloalkyl, $C_2$-$C_4$-alkenyl, $C_2$-$C_4$-alkynyl (it being possible for these groups to be substituted by halogen), phenyl, which may be substituted by $R^1$;

$R^7$ is $C_1$-$C_4$-alkyl, $C_1$-$C_8$-alkoxy, $C_2$-$C_8$-alkenyloxy, $C_2$-$C_8$-alkynyloxy, $C_1$-$C_4$-alkoxy-$C_1$-$C_8$-alkoxy (it being possible for these groups to be substituted by halogen), halogen;

$R^8$ is H, $R^7$ or $C_1$-$C_{12}$-alkyl, $C_3$-$C_{12}$-cycloalkyl, $C_2$-$C_{12}$-alkenyl, $C_5$-$C_{12}$-cycloalkenyl, $C_3$-$C_{12}$-cycloalkyl-$C_1$-$C_4$-alkyl (it being possible for these groups to be substituted by halogen); phenyl, which may be substituted by $R^5$;

n is 0-4;

m is 0, 1.

Furthermore, the present invention relates to the use of the trifluoromethylthiophene-carboxanilides as fungicides, and to compositions comprising them.

EP-A 0545099 discloses acid anilide derivatives and their use for controlling Botrytis. Thiophenecarboxanilides are not described in this application.

Thiophenecarboxanilide derivatives are known from JP 08092223, JP 092592, JP 092593, JP 01302605, JP 01313402, EP-A 915868 and WO 02/08197.

However, the thiophenecarboxanilide derivatives having fungicidal activity that have been described are, in particular at low application rates, not entirely satisfactory.

It is an object of the present invention to provide novel thiophenecarboxanilide derivatives having improved action, and in particular also at low application rates.

We have found that this object is achieved, surprisingly, by the trifluoromethyl-thiophenecarboxanilides of the formulae I, II and III mentioned above.

The organic moieties mentioned in the definition of the substituents $R^1$ to $R^8$ are—like the term halogen—collective terms for individual enumerations of the individual members. All carbon chains, i.e. all alkyl, haloalkyl, arylalkyl, alkenyl, haloalkenyl, alkynyl and haloalkynyl moieties, can be straight-chain or branched. Halogenated substituents preferably carry one to five identical or different halogen atoms. The term halogen denotes in each case fluorine, chlorine, bromine or iodine.

Examples of other meanings are:

$C_1$-$C_4$-alkyl and the $C_1$-$C_4$-alkyl moieties in $C_1$-$C_4$-alkoxy: $CH_3$, $C_2H_5$, $CH_2$—$C_2H_5$, $CH(CH_3)_2$, n-butyl, $CH(CH_3)$—$C_2H_5$, $CH_2$—$CH(CH_3)_2$ or $C(CH_3)_3$;

$C_1$-$C_4$-haloalkyl and the $C_1$-$C_4$-haloalkyl moieties in $C_1$-$C_4$-haloalkoxy: a $C_1$-$C_4$-alkyl radical as mentioned above which is partially or fully substituted by fluorine, chlorine, bromine and/or iodine, i.e., for example, $CH_2F$, $CHF_2$, $CF_3$, $CH_2Cl$, $CH(Cl)_2$, $C(Cl)_3$, chlorofluoromethyl, dichlorofluoromethyl, chlorodifluoromethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, $C_2F_5$, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, $CH_2$—$C_2F_5$, $CF_2$—$C_2F_5$, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl or nonafluorobutyl;

$C_1$-$C_{12}$-alkyl and the $C_1$-$C_8$-alkyl moieties in $C_1$-$C_8$-alkoxy: a $C_1$-$C_4$-alkyl radical as mentioned above or, for example, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl or 1-ethyl-2-methylpropyl, preferably $CH_3$, $C_2H_5$, $CH_2$-$C_2H_5$, $CH(CH_3)_2$, n-butyl, $C(CH_3)_3$, n-pentyl, n-hexyl, n-heptyl, n-octyl, n-nonyl, n-decyl, n-undecyl or n-dodecyl;

$C_1$-$C_{12}$-haloalkyl and the $C_1$-$C_8$-haloalkyl moieties in $C_1$-$C_8$-haloalkoxy: a $C_1$-$C_{12}$-alkyl radical as mentioned above which is partially or fully substituted by fluorine, chlorine, bromine and/or iodine, i.e., for example, one of the radicals mentioned under $C_1$-$C_4$-haloalkyl or 5-fluoro-1-pentyl, 5-chloro-1-pentyl, 5-bromo-1-pentyl, 5-iodo-1-pentyl, 5,5,5-trichloro-1-pentyl, undecafluoropentyl, 6-fluoro-1-hexyl, 6-chloro-1-hexyl, 6-bromo-1-hexyl, 6-iodo-1-hexyl, 6,6,6-trichloro-1-hexyl or dodecafluorohexyl;

$C_2$-$C_4$-alkenyl: unsaturated straight-chain or branched hydrocarbon radicals having 2 to 4 carbon atoms and a double bond in any position, for example ethenyl, 1-propenyl, 2-propenyl, 1-methylethenyl, 1-buten-1-yl, 1-buten-2-yl, 1-buten-3-yl, 2-buten-1-yl, 1-methylprop-1-en-1-yl, 2-methylprop-1-en-1-yl, 1-methylprop-2-en-1-yl, 2-methylprop-2-en-1-yl;

$C_2$-$C_{12}$-alkenyl and the $C_2$-$C_8$-alkenyl moieties in $C_2$-$C_8$-alkenyloxy: $C_2$-$C_4$-alkenyl and also n-penten-1-yl, n-penten-2-yl, n-penten-3-yl, n-penten-4-yl, 1-methylbut-1-en-1-yl, 2-methylbut-1-en-1-yl, 3-methylbut-1-en-1-yl, 1-methylbut-2-en-1-yl, 2-methylbut-2-en-1-yl, 3-methylbut-2-en-1-yl, 1-methylbut-3-en-1-yl, 2-methylbut-3-en-1-yl, 3-methylbut-3-en-1-yl, 1,1-dimethylprop-2-en-1-yl, 1,2-dimethylprop-1-en-1-yl, 1,2-dimethylprop-2-en-1-yl, 1-ethylprop-1-en-2-yl, 1-ethylprop-2-en-1-yl, n-hex-1-en-1-yl, n-hex-2-en-1-yl, n-hex-3-en-1-yl, n-hex-4-en-1-yl, n-hex-5-en-1-yl, 1-methylpent-1-en-1-yl, 2-methylpent-1-en-1-yl, 3-methylpent-1-en-1-yl, 4-methylpent-1-en-1-yl, 1-methylpent-2-en-1-yl, 2-methylpent-2-en-1-yl, 3-methylpent-2-en-1-yl, 4-methylpent-2-en-1-yl, 1-methylpent-3-en-1-yl, 2-methylpent-3-en-1-yl, 3-methylpent-3-en-1-yl, 4-methylpent-3-en-1-yl, 1-methylpent-4-en-1-yl, 2-methylpent-4-en-1-yl, 3-methylpent-4-en-1-yl, 4-methylpent-4-en-1-yl, 1,1-dimethylbut-2-en-1-yl, 1,1-dimethylbut-3-en-1-yl, 1,2-dimethylbut-1-en-1-yl, 1,2-dimethylbut-2-en-1-yl, 1,2-dimethylbut-3-en-1-yl, 1,3-dimethylbut-1-en-1-yl, 1,3-dimethylbut-2-en-1-yl, 1,3-dimethylbut-3-en-1-yl, 2,2-dimethylbut-3-en-1-yl, 2,3-dimethylbut-1-en-1-yl, 2,3-dimethylbut-2-en-1-yl, 2,3-dimethylbut-3-en-1-yl, 3,3-dimethylbut-1-en-1-yl, 3,3-dimethylbut-2-en-1-yl, 1-ethylbut-1-en-1-yl, 1-ethylbut-2-en-1-yl, 1-ethylbut-3-en-1-yl, 2-ethylbut-1-en-1-yl, 2-ethylbut-2-en-1-yl, 2-ethylbut-3-en-1-yl, 1,1,2-trimethylprop-2-en-1-yl, 1-ethyl-1-methylprop-2-en-1-yl, 1-ethyl-2-methylprop-1-en-1-yl or 1-ethyl-2-methylprop-2-en-1-yl;

$C_2$-$C_4$-haloalkenyl: unsaturated straight-chain or branched hydrocarbon radicals having 2 to 4 carbon atoms and a double bond in any position (as mentioned above), where in these groups some or all of the hydrogen atoms are replaced by halogen atoms as mentioned above, in particular by fluorine, chlorine and bromine, i.e., for example, 2-chloroallyl, 3-chloroallyl, 2,3-dichloroallyl, 3,3-dichloroallyl, 2,3,3-trichloroallyl, 2,3-dichlorobut-2-enyl, 2-bromoallyl, 3-bromoallyl, 2,3-dibromoallyl, 3,3-dibromoallyl, 2,3,3-tribromoalkyl or 2,3-dibromobut-2-enyl;

$C_2$-$C_{12}$-haloalkenyl and the haloalkenyl moieties of $C_2$-$C_8$-haloalkenyloxy: $C_2$-$C_{12}$-alkenyl as mentioned above which is partially or fully substituted by fluorine, chlorine, bromine and/or iodine, for example the radicals mentioned under $C_2$-$C_4$-haloalkenyl;

$C_2$-$C_4$-alkynyl: straight-chain or branched hydrocarbon groups having 2 to 4 carbon atoms and a triple bond in any position, for example ethynyl, 1-propynyl, 2-propynyl (=propargyl), 1-butynyl, 2-butynyl, 3-butynyl and 1-methyl-2-propynyl;

$C_2$-$C_{12}$-alkynyl and the $C_2$-$C_8$-alkynyl moieties in $C_2$-$C_8$-alkynyloxy: straight-chain or branched hydrocarbon groups having 2 to 12 carbon atoms and a triple bond in any position, for example ethynyl, prop-1-yn-1-yl, prop-2-yn-1-yl, n-but-1-yn-1-yl, n-but-1-yn-3-yl, n-but-1-yn-4-yl, n-but-2-yn-1-yl, n-pent-1-yn-1-yl, n-pent-1-yn-3-yl, n-pent-1-yn-4-yl, n-pent-1-yn-5-yl, n-pent-2-yn-1-yl, n-pent-2-yn-4-yl, n-pent-2-yn-5-yl, 3-methylbut-1-yn-3-yl, 3-methylbut-1-yn-4-yl, n-hex-1-yn-1-yl, n-hex-1-yn-3-yl, n-hex-1-yn-4-yl, n-hex-1-yn-5-yl, n-hex-1-yn-6-yl, n-hex-2-yn-1-yl, n-hex-2-yn-4-yl, n-hex-2-yn-5-yl, n-hex-2-yn-6-yl, n-hex-3-yn-1-yl, n-hex-3-yn-2-yl, 3-methylpent-1-yn-1-yl, 3-methylpent-1-yn-3-yl, 3-methylpent-1-yn-4-yl, 3-methylpent-1-yn-5-yl, 4-methylpent-1-yn-1-yl, 4-methylpent-2-yn-4-yl and 4-methylpent-2-yn-5-yl, preferably prop-2-yn-1-yl;

$C_2$-$C_4$-haloalkynyl: unsaturated straight-chain or branched hydrocarbon radicals having 2 to 4 carbon atoms and a triple bond in any position (as mentioned above), where in these groups some or all of the hydrogen atoms may be replaced by halogen atoms as mentioned above, in particular by fluorine, chlorine and bromine, i.e., for example, 1,1-difluoroprop-2-yn-1-yl, 4-fluorobut-2-yn-1-yl, 4-chlorobut-2-yn-1-yl, 1,1-difluorobut-2-yn-1-yl, 5-fluoropent-3-yn-1-yl or 6-fluorohex-4-yn-1-yl;

$C_2$-$C_{12}$-haloalkynyl and the $C_2$-$C_8$-haloalkynyl moieties in $C_2$-$C_8$-haloalkynyloxy: $C_2$-$C_{12}$-alkynyl as mentioned above which is partially or fully substituted by fluorine, chlorine, bromine and/or iodine, for example the radicals mentioned under $C_2$-$C_4$-haloalkynyl;

$C_1$-$C_4$-alkoxy: $OCH_3$, $OC_2H_5$, $OCH_2$—$C_2H_5$, $OCH(CH_3)_2$, n-butoxy, $OCH(CH_3)$—$C_2H_5$, $OCH_2$—$CH(CH_3)_2$ or $C(CH_3)_3$, preferably $OCH_3$, $OC_2H_5$ or $OCH(CH_3)_2$;

$C_1$-$C_4$-haloalkoxy: a $C_1$-$C_4$-alkoxy radical as mentioned above which is partially or fully substituted by fluorine, chlorine, bromine and/or iodine, i.e., for example, $OCH_2F$, $OCHF_2$, $OCF_3$, $OCH_2Cl$, $OCH(Cl)_2$, $OC(Cl)_3$, chlorofluoromethoxy, dichlorofluoromethoxy, chlorodifluoromethoxy, 2-fluoroethoxy, 2-chloroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, $OC_2F_5$, 2-fluoropropoxy, 3-fluoropropoxy, 2,2-difluoropropoxy, 2,3-difluoropropoxy, 2-chloropropoxy, 3-chloropropoxy, 2,3-dichloropropoxy, 2-bromopropoxy, 3-bromopropoxy, 3,3,3-trifluoropropoxy, 3,3,3-trichloropropoxy, $OCH_2$—$C_2F_5$, $OCF_2$—$C_2F_5$, 1-($CH_2F$)-2-fluoroethoxy, 1-($CH_2Cl$)-2-chloroethoxy, 1-($CH_2Br$)-2-bromoethoxy, 4-fluorobutoxy, 4-chlorobutoxy, 4-bromobutoxy or nonafluorobutoxy, preferably $OCHF_2$, $OCF_3$, dichlorofluoromethoxy, chlorodifluoromethoxy or 2,2,2-trifluoroethoxy;

$C_1$-$C_8$-alkoxy: a $C_1$-$C_4$-alkoxy radical as mentioned above or, for example, n-pentoxy, 1-methylbutoxy, 2-methylbutoxy, 3-methylbutoxy, 2,2-dimethylpropoxy, 1-ethylpropoxy, n-hexoxy, 1,1-dimethylpropoxy, 1,2-dimethylpropoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy or 1-ethyl-2-methylpropoxy, preferably OCH$_3$, OC$_2$H$_5$, OCH$_2$—C$_2$H$_5$, OCH(CH$_3$)$_2$, n-butoxy, OC(CH$_3$)$_3$, n-pentoxy or n-hexoxy;

C$_1$-C$_8$-haloalkoxy: a C$_1$-C$_8$-alkoxy radical as mentioned above which is partially or fully substituted by fluorine, chlorine, bromine and/or iodine, i.e., for example, one of the radicals mentioned under C$_1$-C$_4$-haloalkoxy or 5-fluoro-1-pentoxy, 5-chloro-1-pentoxy, 5-bromo-1-pentoxy, 5-iodo-1-pentoxy, 5,5,5-trichloro-1-pentoxy, undecafluoropentoxy, 6-fluoro-1-hexoxy, 6-chloro-1-hexoxy, 6-bromo-1-hexoxy, 6-iodo-1-hexoxy, 6,6,6-trichloro-1-hexoxy or dodecafluorohexoxy;

C$_3$-C$_{12}$-cycloalkyl: cyclopropyl, cyclobutyl, cyclopentyl, cyclohexyl, cycloheptyl or cyclooctyl;

C$_3$-C$_{12}$-cycloalkyl-C$_1$-C$_4$-alkyl: C$_1$-C$_4$-alkyl which is substituted by C$_3$-C$_{12}$-cycloalkyl, for example cyclopropylmethyl, cyclobutylmethyl, cyclopentylmethyl, cyclohexylmethyl, cycloheptylmethyl, cyclooctylmethyl, 2-(cyclopropyl)ethyl, 2-(cyclobutyl)ethyl, 2-(cyclopentyl)ethyl, 2-(cyclohexyl)ethyl, 2-(cycloheptyl)ethyl, 2-(cyclooctyl)ethyl, 3-(cyclopropyl)propyl, 3-(cyclobutyl)propyl, 3-(cyclopentyl)propyl, 3-(cyclohexyl)propyl, 3-(cycloheptyl)propyl, 3-(cyclooctyl)propyl, 4-(cyclopropyl)butyl, 4-(cyclobutyl)butyl, 4-(cyclopentyl)butyl, 4-(cyclohexyl)butyl, 4-(cycloheptyl)butyl, 4-(cyclooctyl)butyl;

phenyl-C$_1$-C$_6$-alkyl: C$_1$-C$_6$-alkyl which is substituted by phenyl, for example benzyl, 1- or 2-phenylethyl, 1-, 2- or 3-phenylpropyl;

phenyloxy-C$_1$-C$_6$-alkyl: C$_1$-C$_6$-alkyl which is substituted by phenoxy, for example phenoxymethyl, 1- or 2-phenoxyethyl, 1-, 2- or 3-phenoxypropyl;

phenyl-C$_2$-C$_6$-alkenyl: C$_2$-C$_6$-alkenyl which is substituted by phenyl, for example 1- or 2-phenylethenyl, 1-phenylprop-2-en-1-yl, 3-phenylprop-1-en-1-yl, 3-phenylprop-2-en-1-yl, 4-phenylbut-1-en-1-yl or 4-phenylbut-2-en-1-yl;

phenyl-C$_2$-C$_6$-alkynyl: C$_2$-C$_6$-alkynyl which is substituted by phenyl, for example 1-phenylprop-2-yn-1-yl, 3-phenylprop-1-yn-1-yl, 3-phenylprop-2-yn-1-yl, 4-phenylbut-1-yn-1-yl or 4-phenylbut-2-yn-1-yl.

Preference is given to trifluoromethylthiophenecarboxanilides of the formulae I, II and III in which the substituents are as defined below:

R$^1$ is halogen or C$_1$-C$_4$-alkyl, which may be substituted by halogen, is particularly preferably fluorine, chlorine, bromine or methyl;

R$^2$ is H, methyl, OH or methoxy;

R$^3$ is C$_1$-C$_{12}$-alkyl, C$_3$-C$_{12}$-cycloalkyl, C$_2$-C$_{12}$-alkenyl, C$_5$-C$_{12}$-cycloalkenyl, C$_2$-C$_{12}$-alkynyl, it being possible for these groups to be substituted by halogen and C$_1$-C$_4$-alkyl; phenyl, phenyl-C$_1$-C$_6$-alkyl, it being possible for the phenyl ring to be substituted by R$^5$; or —C(C$_1$-C$_4$-alkyl)=NO—R$^6$, it being possible for the C$_1$-C$_4$-alkyl group to be substituted by halogen;

X is a direct bond or O, is particularly preferably a direct bond, is furthermore particularly preferably O;

R$^4$ is halogen, C$_1$-C$_4$-alkyl, C$_1$-C$_4$-alkoxy (it being possible for these groups to be substituted by halogen), is particularly preferably fluorine, chlorine, methyl, trifluoromethyl or methoxy, trifluoromethoxy, difluoromethyl;

R$^5$ is H, C$_1$-C$_4$-alkyl, C$_3$-C$_6$-cycloalkyl, C$_1$-C$_4$-alkoxy, C$_2$-C$_4$-alkenyl, C$_2$-C$_4$-alkynyl (it being possible for these groups to be substituted by halogen), halogen, nitro, CN, phenyl (which may be substituted by R$^1$), phenoxy (which may be substituted by R$^1$), C$_1$-C$_6$-alkylphenyl, where the alkyl moiety may be substituted by halogen and the phenyl ring may be substituted by R$^1$;

R$^6$ is C$_1$-C$_4$-alkyl, C$_3$-C$_6$-cycloalkyl, C$_2$-C$_4$-alkenyl, C$_2$-C$_4$-alkynyl (it being possible for these groups to be substituted by halogen), phenyl which may be substituted by R$^1$;

R$^7$ is C$_1$-C$_4$-alkyl, C$_1$-C$_8$-alkoxy, C$_2$-C$_8$-alkenyloxy, C$_2$-C$_8$-alkynyloxy, C$_1$-C$_4$-alkoxy-C$_1$-C$_8$-alkoxy (it being possible for these groups to be substituted by halogen), halogen;

R$^8$ is H, R$^7$ or C$_1$-C$_{12}$-alkyl, C$_3$-C$_{12}$-cycloalkyl, C$_2$-C$_{12}$-alkenyl, C$_5$-C$_{12}$-cycloalkenyl, C$_3$-C$_{12}$-cycloalkyl-C$_1$-C$_4$-alkyl (it being possible for these groups to be substituted by halogen);

phenyl, which may be substituted by R$^5$;

n is 0-4, preferably 0 or 1, particularly preferably 0;

m is 0 or 1, particularly preferably 0.

Particular preference is given to trifluoromethylthiophenecarboxanilides of the formulae Ia, Ib, IIa, IIb, IIIa and IIIb Ia
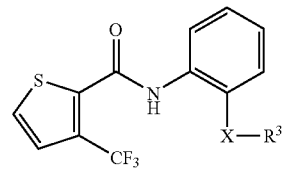

IIa
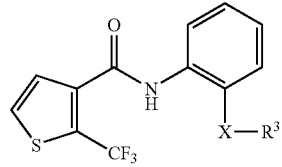

IIIa
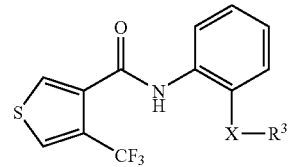

Ib
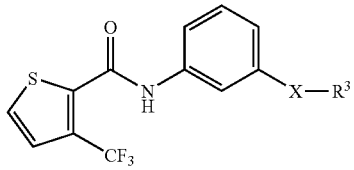

IIb
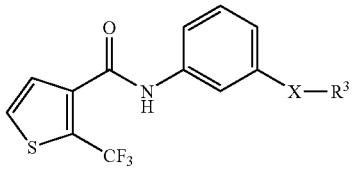

IIIb
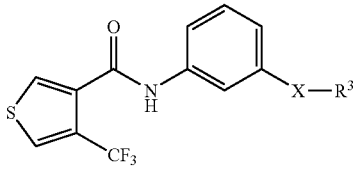

in which the substituents are as defined below:

R$^3$ is C$_1$-C$_{12}$-alkyl, C$_3$-C$_{12}$-cycloalkyl, C$_2$-C$_{12}$-alkenyl, C$_5$-C$_{12}$-cycloalkenyl, C$_2$-C$_{12}$-alkynyl, it being possible for these groups to be substituted by halogen or $C_1$-$C_4$-alkyl; phenyl, phenyl-$C_1$-$C_6$-alkyl, it being possible for the phenyl ring to be substituted by $R^5$, or —$C(C_1$-$C_4$-alkyl)=NO—$R^6$, it being possible for the $C_1$-$C_4$-alkyl group to be substituted by halogen;

X is a direct bond or O, particularly preferably a direct bond, furthermore particularly preferably O.

With a view to their use as fungicides and active compounds for controlling pests, particular preference is given to the individual compounds compiled in tables 1 to 120 below, which are embraced by the formulae Ia, Ib, Ic, Id, IIa, IIb, IIc, IId, IIIa, IIIb, IIIc and IIId.

TABLE A

| No. | $R^3$ |
|---|---|
| 1 | $CH_3$ |
| 2 | $C_2H_5$ |
| 3 | n-$C_3H_7$ |
| 4 | i-$C_3H_7$ |
| 5 | cyclopropyl |
| 6 | n-$C_4H_9$ |
| 7 | s-$C_4H_9$ |
| 8 | i-$C_4H_9$ |
| 9 | t-$C_4H_9$ |
| 10 | n-$C_5H_{11}$ |
| 11 | i-$C_5H_{11}$ |
| 12 | neo-$C_5H_{11}$ |
| 13 | cyclopentyl |
| 14 | n-$C_6H_{13}$ |
| 15 | cyclohexyl |
| 16 | cyclobutyl |
| 17 | $CH_2CH_2Cl$ |
| 18 | $(CH_2)_4Cl$ |
| 19 | 2-methoxyeth-1-yl |
| 20 | 2-ethoxyeth-1-yl |
| 21 | 2-isopropoxyeth-1-yl |
| 22 | 2-vinyloxyeth-1-yl |
| 23 | allyloxyeth-1-yl |
| 24 | 2-trifluoromethoxyeth-1-yl |
| 25 | prop-2-yn-1-yl |
| 26 | but-2-yn-1-yl |
| 27 | but-3-yn-1-yl |
| 28 | 3-chloroprop-2-yn-1-yl |
| 29 | benzyl |
| 30 | 1-naphthyl-$CH_2$ |
| 31 | 2-naphthyl-$CH_2$ |
| 32 | 2-phenoxyeth-1-yl |
| 33 | 2-(2'-chlorophenoxy)eth-1-yl |
| 34 | 2-(3'-chlorophenoxy)eth-1-yl |
| 35 | 2-(4'-chlorophenoxy)eth-1-yl |
| 36 | 2-(3',5'-dichlorophenoxy)eth-1-yl |
| 37 | 2-(2'-cyanophenoxy)eth-1-yl |
| 38 | 2-(3'-cyanophenoxy)eth-1-yl |
| 39 | 2-(4'-cyanophenoxy)eth-1-yl |
| 40 | 2-(2'-methylphenoxy)eth-1-yl |
| 41 | 2-(3'-methylphenoxy)eth-1-yl |
| 42 | 2-(4'-methylphenoxy)eth-1-yl |
| 43 | 2-(3'-t-butylphenoxy)eth-1-yl |
| 44 | 2-(4'-t-butylphenoxy)eth-1-yl |
| 45 | 2-(2'-nitrophenoxy)eth-1-yl |
| 46 | 2-(3'-nitrophenoxy)eth-1-yl |
| 47 | 2-(4'-nitrophenoxy)eth-1-yl |
| 48 | 2-(2'-methoxyphenoxy)eth-1-yl |
| 49 | 2-(3'-methoxyphenoxy)eth-1-yl |
| 50 | 2-(4'-methoxyphenoxy)eth-1-yl |
| 51 | 2-(2'-trifluoromethylphenoxy)eth-1-yl |
| 52 | 2-(3'-trifluoromethylphenoxy)eth-1-yl |
| 53 | 2-(4'-trifluoromethylphenoxy)eth-1-yl |
| 54 | 2-phenyleth-1-yl |
| 55 | 2-(2'-chlorophenyl)eth-1-yl |
| 56 | 2-(3'-chlorophenyl)eth-1-yl |
| 57 | 2-(4'-chlorophenyl)eth-1-yl |
| 58 | 2-(3',5'-dichlorophenyl)eth-1-yl |
| 59 | 2-(2'-cyanophenyl)eth-1-yl |
| 60 | 2-(3'-cyanophenyl)eth-1-yl |

TABLE A-continued

| No. | $R^3$ |
|---|---|
| 61 | 2-(4'-cyanophenyl)eth-1-yl |
| 62 | 2-(2'-methylphenyl)eth-1-yl |
| 63 | 2-(3'-methylphenyl)eth-1-yl |
| 64 | 2-(4'-methylphenyl)eth-1-yl |
| 65 | 2-(2'-methoxyphenyl)eth-1-yl |
| 66 | 2-(3'-methoxyphenyl)eth-1-yl |
| 67 | 2-(4'-methoxyphenyl)eth-1-yl |
| 68 | 2-(2'-trifluoromethylphenyl)eth-1-yl |
| 69 | 2-(3'-trifluoromethylphenyl)eth-1-yl |
| 70 | 2-(4'-trifluoromethylphenyl)eth-1-yl |
| 71 | $C_6H_5$ |
| 72 | 2-F—$C_6H_4$ |
| 73 | 3-F—$C_6H_4$ |
| 74 | 4-F—$C_6H_4$ |
| 75 | 2,3-$F_2$—$C_6H_3$ |
| 76 | 2,4-$F_2$—$C_6H_3$ |
| 77 | 2,5-$F_2$—$C_6H_3$ |
| 78 | 2,6-$F_2$—$C_6H_3$ |
| 79 | 3,4-$F_2$—$C_6H_3$ |
| 80 | 3,5-$F_2$—$C_6H_3$ |
| 81 | 2-Cl—$C_6H_4$ |
| 82 | 3-Cl—$C_6H_4$ |
| 83 | 4-Cl—$C_6H_4$ |
| 84 | 2,3-$Cl_2$—$C_6H_3$ |
| 85 | 2,4-$Cl_2$—$C_6H_3$ |
| 86 | 2,5-$Cl_2$—$C_6H_3$ |
| 87 | 2,6-$Cl_2$—$C_6H_3$ |
| 88 | 3,4-$Cl_2$—$C_6H_3$ |
| 89 | 3,5-$Cl_2$—$C_6H_3$ |
| 90 | 2,3,4-$Cl_3$—$C_6H_2$ |
| 91 | 2,3,5-$Cl_3$—$C_6H_2$ |
| 92 | 2,3,6-$Cl_3$—$C_6H_2$ |
| 93 | 2,4,5-$Cl_3$—$C_6H_2$ |
| 94 | 2,4,6-$Cl_3$—$C_6H_2$ |
| 95 | 3,4,5-$Cl_3$—$C_6H_2$ |
| 96 | 2-Br—$C_6H_4$ |
| 97 | 3-Br—$C_6H_4$ |
| 98 | 4-Br—$C_6H_4$ |
| 99 | 2,3-$Br_2$—$C_6H_3$ |
| 100 | 2,4-$Br_2$—$C_6H_3$ |
| 101 | 2,5-$Br_2$—$C_6H_3$ |
| 102 | 2,6-$Br_2$—$C_6H_3$ |
| 103 | 3,4-$Br_2$—$C_6H_3$ |
| 104 | 3,5-$Br_2$—$C_6H_3$ |
| 105 | 2-F, 3-Cl—$C_6H_3$ |
| 106 | 2-F, 4-Cl—$C_6H_3$ |
| 107 | 2-F, 5-Cl—$C_6H_3$ |
| 108 | 2-F, 3-Br—$C_6H_3$ |
| 109 | 2-F, 4-Br—$C_6H_3$ |
| 110 | 2-F, 5-Br—$C_6H_3$ |
| 111 | 2-Cl, 3-Br—$C_6H_3$ |
| 112 | 2-Cl, 4-Br—$C_6H_3$ |
| 113 | 2-Cl, 5-Br—$C_6H_3$ |
| 114 | 3-F, 4-Cl—$C_6H_3$ |
| 115 | 3-F, 5-Cl—$C_6H_3$ |
| 116 | 3-F, 6-Cl—$C_6H_3$ |
| 117 | 3-F, 4-Br—$C_6H_3$ |
| 118 | 3-F, 5-Br—$C_6H_3$ |
| 119 | 3-F, 6-Br—$C_6H_3$ |
| 120 | 3-Cl, 4-Br—$C_6H_3$ |
| 121 | 3-Cl, 5-Br—$C_6H_3$ |
| 122 | 3-Cl, 6-Br—$C_6H_3$ |
| 123 | 4-F, 5-Cl—$C_6H_3$ |
| 124 | 4-F, 6-Cl—$C_6H_3$ |
| 125 | 4-F, 5-Br—$C_6H_3$ |
| 126 | 4-F, 6-Br—$C_6H_3$ |
| 127 | 4-Cl, 5-Br—$C_6H_3$ |
| 128 | 5-F, 6-Cl—$C_6H_3$ |
| 129 | 5-F, 6-Br—$C_6H_3$ |
| 130 | 5-Cl, 6-Br—$C_6H_3$ |
| 131 | 3-Br, 4-Cl, 5-Br—$C_6H_2$ |
| 132 | 2-CN—$C_6H_4$ |
| 133 | 3-CN—$C_6H_4$ |
| 134 | 4-CN—$C_6H_4$ |
| 135 | 2-$NO_2$—$C_6H_4$ |
| 136 | 3-$NO_2$—$C_6H_4$ |
| 137 | 4-$NO_2$—$C_6H_4$ |

TABLE A-continued

| No. | R³ |
|---|---|
| 138 | 2-CH₃—C₆H₄ |
| 139 | 3-CH₃—C₆H₄ |
| 140 | 4-CH₃—C₆H₄ |
| 141 | 2,3-(CH₃)₂—C₆H₃ |
| 142 | 2,4-(CH₃)₂—C₆H₃ |
| 143 | 2,5-(CH₃)₂—C₆H₃ |
| 144 | 2,6-(CH₃)₂—C₆H₃ |
| 145 | 3,4-(CH₃)₂—C₆H₃ |
| 146 | 3,5-(CH₃)₂—C₆H₃ |
| 147 | 2-C₂H₅—C₆H₄ |
| 148 | 3-C₂H₅—C₆H₄ |
| 149 | 4-C₂H₅—C₆H₄ |
| 150 | 2-i-C₃H₇—C₆H₄ |
| 151 | 3-i-C₃H₇—C₆H₄ |
| 152 | 4-i-C₃H₇—C₆H₄ |
| 153 | 3-tert-C₄H₉—C₆H₄ |
| 154 | 4-tert-C₄H₉—C₆H₄ |
| 155 | 2-vinyl-C₆H₄ |
| 156 | 3-vinyl-C₆H₄ |
| 157 | 4-vinyl-C₆H₄ |
| 158 | 2-allyl-C₆H₄ |
| 159 | 3-allyl-C₆H₄ |
| 160 | 4-allyl-C₆H₄ |
| 161 | 2-C₆H₅—C₆H₄ |
| 162 | 3-C₆H₅—C₆H₄ |
| 163 | 4-C₆H₅—C₆H₄ |
| 164 | 3-CH₃, 5-tert-C₄H₉—C₆H₃ |
| 165 | 2-OH—C₆H₄ |
| 166 | 3-OH—C₆H₄ |
| 167 | 4-OH—C₆H₄ |
| 168 | 2-OCH₃—C₆H₄ |
| 169 | 3-OCH₃—C₆H₄ |
| 170 | 4-OCH₃—C₆H₄ |
| 171 | 2,3-(OCH₃)₂—C₆H₃ |
| 172 | 2,4-(OCH₃)₂—C₆H₃ |
| 173 | 2,5-(OCH₃)₂—C₆H₃ |
| 174 | 3,4-(OCH₃)₂—C₆H₃ |
| 175 | 3,5-(OCH₃)₂—C₆H₃ |
| 176 | 3,4,5-(OCH₃)₃—C₆H₂ |
| 177 | 2-OC₂H₅—C₆H₄ |
| 178 | 3-OC₂H₅—C₆H₄ |
| 179 | 4-OC₂H₅—C₆H₄ |
| 180 | 2-O-(n-C₃H₇)—C₆H₄ |
| 181 | 3-O-(n-C₃H₇)—C₆H₄ |
| 182 | 4-O-(n-C₃H₇)—C₆H₄ |
| 183 | 2-O-(i-C₃H₇)—C₆H₄ |
| 184 | 3-O-(i-C₃H₇)—C₆H₄ |
| 185 | 4-O-(i-C₃H₇)—C₆H₄ |
| 186 | 4-O-(n-C₄H₉)—C₆H₄ |
| 187 | 3-O-(t-C₄H₉)—C₆H₄ |
| 188 | 4-O-(t-C₄H₉)—C₆H₄ |
| 189 | 2-O-allyl-C₆H₄ |
| 190 | 3-O-allyl-C₆H₄ |
| 191 | 4-O-allyl-C₆H₄ |
| 192 | 2-CF₃—C₆H₄ |
| 193 | 3-CF₃—C₆H₄ |
| 194 | 4-CF₃—C₆H₄ |
| 195 | 2-acetyl-C₆H₄ |
| 196 | 3-acetyl-C₆H₄ |
| 197 | 4-acetyl-C₆H₄ |
| 198 | 2-methoxycarbonyl-C₆H₄ |
| 199 | 3-methoxycarbonyl-C₆H₄ |
| 200 | 4-methoxycarbonyl-C₆H₄ |
| 201 | 2-aminocarbonyl-C₆H₄ |
| 202 | 3-aminocarbonyl-C₆H₄ |
| 203 | 4-aminocarbonyl-C₆H₄ |
| 204 | 2-dimethylaminocarbonyl-C₆H₄ |
| 205 | 3-dimethylaminocarbonyl-C₆H₄ |
| 206 | 4-dimethylaminocarbonyl-C₆H₄ |
| 207 | 2-(N-methylaminocarbonyl)-C₆H₄ |
| 208 | 3-(N-methylaminocarbonyl)-C₆H₄ |
| 209 | 4-(N-methylaminocarbonyl)-C₆H₄ |
| 210 | 2-H₂N—C₆H₄ |
| 211 | 3-H₂N—C₆H₄ |
| 212 | 4-H₂N—C₆H₄ |
| 213 | 2-aminothiocarbonyl-C₆H₄ |
| 214 | 3-aminothiocarbonyl-C₆H₄ |
| 215 | 4-aminothiocarbonyl-C₆H₄ |
| 216 | 2-methoxyiminomethyl-C₆H₄ |
| 217 | 3-methoxyiminomethyl-C₆H₄ |
| 218 | 4-methoxyiminomethyl-C₆H₄ |
| 219 | 3,4-methylenedioxy-C₆H₃ |
| 220 | 3,4-difluoromethylenedioxy-C₆H₃ |
| 221 | 2,3-methylenedioxy-C₆H₃ |
| 222 | 2-(1'-methoxyiminoeth-1'-yl)-C₆H₄ |
| 223 | 3-(1'-methoxyiminoeth-1'-yl)-C₆H₄ |
| 224 | 4-(1'-methoxyiminoeth-1'-yl)-C₆H₄ |
| 225 | 2-SCH₃—C₆H₄ |
| 226 | 3-SCH₃—C₆H₄ |
| 227 | 4-SCH₃—C₆H₄ |
| 228 | 2-SO₂CH₃—C₆H₄ |
| 229 | 3-SO₂CH₃—C₆H₄ |
| 230 | 4-SO₂CH₃—C₆H₄ |
| 231 | 2-OCF₃—C₆H₄ |
| 232 | 3-OCF₃—C₆H₄ |
| 233 | 4-OCF₃—C₆H₄ |
| 234 | 2-OCHF₂—C₆H₄ |
| 235 | 3-OCHF₂—C₆H₄ |
| 236 | 4-OCHF₂—C₆H₄ |
| 237 | 3-CF₃, 4-OCF₃—C₆H₃ |
| 238 | 2-NHCH₃—C₆H₄ |
| 239 | 3-NHCH₃—C₆H₄ |
| 240 | 4-NHCH₃—C₆H₄ |
| 241 | 2-N(CH₃)₂—C₆H₄ |
| 242 | 3-N(CH₃)₂—C₆H₄ |
| 243 | 4-N(CH₃)₂—C₆H₄ |
| 244 | 2-ethoxycarbonyl-C₆H₄ |
| 245 | 3-ethoxycarbonyl-C₆H₄ |
| 246 | 4-ethoxycarbonyl-C₆H₄ |
| 247 | 2-CH₂CH₂F—C₆H₄ |
| 248 | 3-CH₂CH₂F—C₆H₄ |
| 249 | 4-CH₂CH₂F—C₆H₄ |
| 250 | 2-CH₂CF₃—C₆H₄ |
| 251 | 3-CH₂CF₃—C₆H₄ |
| 252 | 4-CH₂CF₃—C₆H₄ |
| 253 | 2-CF₂CHF₂—C₆H₄ |
| 254 | 3-CF₂CHF₂—C₆H₄ |
| 255 | 4-CF₂CHF₂—C₆H₄ |
| 256 | 2-CHF₂—C₆H₄ |
| 257 | 3-CHF₂—C₆H₄ |
| 258 | 4-CHF₂—C₆H₄ |
| 259 | 2-(1'-oxo-n-prop-1-yl)-C₆H₄ |
| 260 | 3-(1'-oxo-n-prop-1-yl)-C₆H₄ |
| 261 | 4-(1'-oxo-n-prop-1-yl)-C₆H₄ |
| 262 | 2-(1'-oxoisoprop-1-yl)-C₆H₄ |
| 263 | 3-(1'-oxoisoprop-1-yl)-C₆H₄ |
| 264 | 4-(1'-oxoisoprop-1-yl)-C₆H₄ |
| 265 | 3-cyclopropyl-C₆H₄ |
| 266 | 4-cyclopropyl-C₆H₄ |
| 267 | 4-cyclohexyl-C₆H₄ |
| 268 | —C≡CH |
| 269 | —C≡C—Cl |
| 270 | —C≡C—Br |
| 271 | —C≡C—CH₃ |
| 273 | —C≡C—C₆H₅ |
| 274 | —C≡C-[2-Cl—C₆H₄] |
| 275 | —C≡C-[4-Cl—C₆H₄] |
| 276 | —C≡C-[2,4-Cl₂—C₆H₃] |
| 277 | —C≡C-[2-CH₃—C₆H₄] |
| 278 | —C≡C-[4-CH₃—C₆H₄] |
| 279 | —C≡C-[2,4-(CH₃)₂—C₆H₃] |
| 280 | —C≡C-[2-Cl, 4-CH₃—C₆H₃] |
| 281 | —C≡C-[2-CH₃, 4-Cl—C₆H₃] |
| 282 | —C≡C-[3-CF₃—C₆H₄] |
| 283 | —C≡C-[3-Cl, 5-CF₃—C₆H₃] |
| 284 | —C≡C-[2-OCH₃—C₆H₄] |
| 285 | —C≡C-[4-OCH₃—C₆H₄] |
| 286 | —C≡C-[2,4-(OCH₃)₂—C₆H₃] |
| 287 | —C≡C-[2-Cl, 4-OCH₃—C₆H₃] |
| 288 | —C≡C-[2-OCH₃, 4-Cl—C₆H₃] |
| 289 | —C≡C-[3-OCHF₂—C₆H₄] |
| 290 | —C≡C-[3-Cl, 5-OCHF₂—C₆H₃] |
| 291 | cyclopentyl |
| 292 | 1-CH₃-cyclopentyl |

TABLE A-continued

| No. | R³ |
|---|---|
| 293 | 2-CH₃-cyclopentyl |
| 294 | 3-CH₃-cyclopentyl |
| 295 | 2,3-(CH₃)₂-cyclopentyl |
| 296 | 1-Cl-cyclopentyl |
| 297 | 2-Cl-cyclopentyl |
| 298 | 3-Cl-cyclopentyl |
| 299 | 2-CH₃, 3-Cl-cyclopentyl |
| 300 | 2,3-Cl₂-cyclopentyl |
| 301 | cyclohexyl |
| 302 | 1-CH₃-cyclohexyl |
| 303 | 2-CH₃-cyclohexyl |
| 304 | 3-CH₃-cyclohexyl |
| 305 | 2,3-(CH₃)₂-cyclohexyl |
| 306 | 3,3-(CH₃)₂-cyclohexyl |
| 307 | 1-Cl-cyclohexyl |
| 308 | 2-Cl-cyclohexyl |
| 309 | 3-Cl-cyclohexyl |
| 310 | 2-CH₃, 3-Cl-cyclohexyl |
| 311 | 2,3-Cl₂-cyclohexyl |
| 312 | CH₂—C≡C—H |
| 313 | CH₂—C≡C—Cl |
| 314 | CH₂—C≡C—Br |
| 315 | CH₂—C≡C-J |
| 316 | CH₂—C≡C—CH₃ |
| 317 | CH₂—C≡C—CH₂CH₃ |
| 318 | CH₂CH₂—C≡C—H |
| 319 | CH₂CH₂—C≡C—Cl |
| 320 | CH₂CH₂—C≡C—Br |
| 321 | CH₂CH₂—C≡C-J |
| 322 | CH₂CH₂—C≡C—CH₃ |
| 323 | CH₂CH₂CH₂—C≡C—H |
| 324 | CH₂CH₂CH₂—C≡C—Cl |
| 325 | CH₂CH₂CH₂—C≡C—Br |
| 326 | CH₂CH₂CH₂—C≡C-J |
| 327 | CH₂CH₂CH₂—C≡C—CH₃ |
| 328 | CH(CH₃)—C≡C—H |
| 329 | CH(CH₃)—C≡C—Cl |
| 330 | CH(CH₃)—C≡C—Br |
| 331 | CH(CH₃)—C≡C-J |
| 332 | CH(CH₃)—C≡C—CH₃ |
| 333 | —C≡C-[4-F—C₆H₄] |
| 334 | n-heptyl |
| 335 | n-octyl |
| 336 | vinyl |
| 337 | 1-methylvinyl |
| 338 | 2-methylvinyl |
| 339 | allyl |
| 340 | 2-methylallyl |
| 341 | 2-ethylallyl |
| 342 | 1-methylallyl |
| 343 | 1-ethylallyl, |
| 344 | 1-methyl-2-butenyl |
| 345 | 1-ethyl-2-butenyl |
| 346 | 1-isopropyl-2-butenyl |
| 347 | 1-n-butyl-2-butenyl |
| 348 | 1-methyl-2-pentyl |
| 349 | 1,4-dimethyl-2-pentenyl |
| 350 | propargyl |
| 351 | 2-butynyl |
| 352 | 3-butynyl |
| 353 | 2-cyclopentenyl |
| 354 | 1-cyclopentenyl |
| 355 | 1-cyclohexenyl |
| 356 | 2-cyclohexenyl |
| 357 | —CH₂F |
| 358 | —CHF₂ |
| 359 | —CF₃ |
| 360 | —CH₂—CHF₂ |
| 361 | —CH₂—CF₃ |
| 362 | —CHF—CF₃ |
| 363 | —CF₂—CHF₂ |
| 364 | —CF₂—CF₃ |
| 365 | CH₂—CF₂—CHF₂ |
| 366 | CH₂—CF₂—CF₃ |
| 367 | CF₂—CF₂—CF₃ |
| 368 | —CF₂—CHF—CF₃ |
| 369 | —CH₂(CF₂)₂—CF₃ |

TABLE A-continued

| No. | R³ |
|---|---|
| 370 | —CF₂(CF₂)₂—CF₃ |
| 371 | —CH₂(CF₂)₃—CF₃ |
| 372 | —CF₂(CF₂)₃—CF₃ |
| 373 | —CF₂—CF₂Omethyl |
| 374 | —CF₂—CF₂Oethyl |
| 375 | CF₂—CF₂O-n-propyl |
| 376 | CF₂—CF₂O-n-butyl |
| 377 | —CF₂—(CF₂)₂Omethyl |
| 378 | —CF₂—(CF₂)₂Oethyl |
| 379 | —CF₂—(CF₂)₂O-n-propyl |
| 380 | —CF₂—(CF₂)₂O-n-butyl |
| 381 | —(CF₂)₂—O—(CF₂)₂Omethyl |
| 382 | —(CF₂)₂—O—(CF₂)₂Oethyl |
| 383 | —(CF₂)₂—O—(CF₂)₂O-n-propyl |
| 384 | —(CF₂)₂—O—(CF₂)₂O-n-butyl |
| 385 | —CH₂—CHCl₂ |
| 386 | —CH₂—CCl₃ |
| 387 | —CCl₂—CHCl₂ |
| 388 | —CH₂CFCl₂ |
| 389 | —CH₂—CClF₂ |
| 390 | —CH₂—CCl₂—CCl₃ |
| 391 | —CH₂—CF₂—CHF—CF₂—CClF₂ |

Table 1:

Compounds of the formula Ia

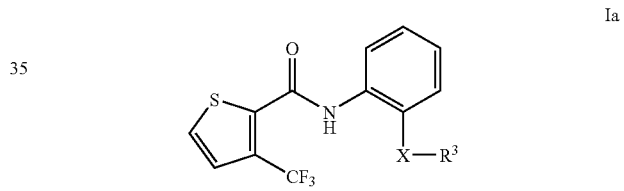

in which X is a direct bond and R³ has one of the meanings given in table A.

Table 2:

Compounds of the formula Ia in which X is O and R³ has one of the meanings given in table A.

Table 3:

Compounds of the formula Ib

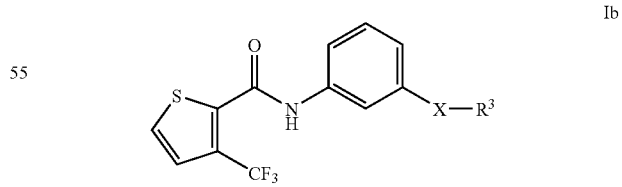

in which X is a direct bond and R³ has one of the meanings given in table A.

Table 4:

Compounds of the formula Ib in which X is O and R³ has one of the meanings given in table A.

Table 5:
Compounds of the formula IIa

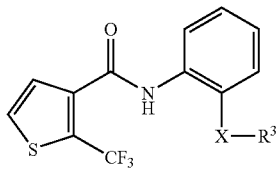

IIa in which X is a direct bond and $R^3$ has one of the meanings given in table A.

Table 6:
Compounds of the formula IIa in which X is O and $R^3$ has one of the meanings given in table A.

Table 7:
Compounds of the formula IIb

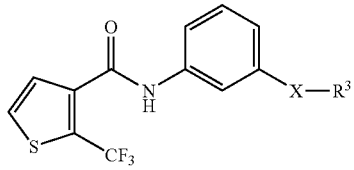

IIb in which X is a direct bond and $R^3$ has one of the meanings given in table A.

Table 8:
Compounds of the formula IIb in which X is O and $R^3$ has one of the meanings given in table A.

Table 9:
Compounds of the formula IIIa

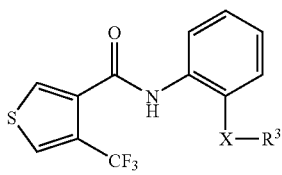

IIIa in which X is a direct bond and $R^3$ has one of the meanings given in table A.

Table 10:
Compounds of the formula IIIa in which X is O and $R^3$ has one of the meanings given in table A.

Table 11:
Compounds of the formula IIIb

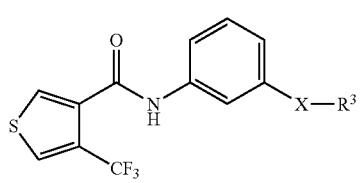

IIIb in which X is a direct bond and $R^3$ has one of the meanings given in table A.

Table 12:
Compounds of the formula IIIb, in which X is O and $R^3$ has one of the meanings given in table A.

Table 13:
Compounds of the formula Ic

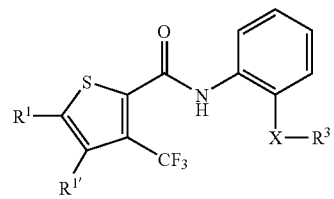

Ic in which
$R^1$ is H, $R^{1'}$ is methyl, X is a direct bond and $R^3$ has one of the meanings given in table A.

Table 14:
Compounds of the formula Ic in which
$R^1$ is H, $R^{1'}$ is fluorine, X is a direct bond and $R^3$ has one of the meanings given in table A.

Table 15:
Compounds of the formula Ic in which
$R^1$ is H, $R^{1'}$ is chlorine, X is a direct bond and $R^3$ has one of the meanings given in table A.

Table 16:
Compounds of the formula Ic in which
$R^1$ is methyl, $R^{1'}$ is H, X is a direct bond and $R^3$ has one of the meanings given in table A.

Table 17:
Compounds of the formula Ic in which
$R^1$ is methyl, $R^{1'}$ is methyl, X is a direct bond and $R^3$ has one of the meanings given in table A.

Table 18:
Compounds of the formula Ic in which
$R^1$ is methyl, $R^{1'}$ is fluorine, X is a direct bond and $R^3$ has one of the meanings given in table A.

Table 19:
Compounds of the formula Ic in which
$R^1$ is methyl, $R^{1'}$ is chlorine, X is a direct bond and $R^3$ has one of the meanings given in table A.

Table 20:
Compounds of the formula Ic in which
$R^1$ is fluorine, $R^{1'}$ is H, X is a direct bond and $R^3$ has one of the meanings given in table A.

Table 21:
Compounds of the formula Ic in which
$R^1$ is fluorine, $R^{1'}$ is methyl, X is a direct bond and $R^3$ has one of the meanings given in table A.

Table 22:
Compounds of the formula Ic in which
$R^1$ is fluorine, $R^{1'}$ is fluorine, X is a direct bond and $R^3$ has one of the meanings given in table A.

Table 23:
Compounds of the formula Ic in which
$R^1$ is fluorine, $R^{1'}$ is chlorine, X is a direct bond and $R^3$ has one of the meanings given in table A.

Table 24:
Compounds of the formula Ic in which
$R^1$ is chlorine, $R^{1'}$ is H, X is a direct bond and $R^3$ has one of the meanings given in table A.
Table 25:
Compounds of the formula Ic in which
$R^1$ is chlorine, $R^{1'}$ is methyl, X is a direct bond and $R^3$ has one of the meanings given in table A.
Table 26:
Compounds of the formula Ic in which
$R^1$ is chlorine, $R^{1'}$ is fluorine, X is a direct bond and $R^3$ has one of the meanings given in
Table 27:
Compounds of the formula Ic in which
$R^1$ is chlorine, $R^{1'}$ is chlorine, X is a direct bond and $R^3$ has one of the meanings given in table A.
Table 28:
Compounds of the formula Ic in which
$R^1$ is H, $R^{1'}$ is methyl, X is O and $R^3$ has one of the meanings given in table A.
Table 29:
Compounds of the formula Ic in which
$R^1$ is H, $R^{1'}$ is fluorine, X is O and $R^3$ has one of the meanings given in table A.
Table 30:
Compounds of the formula Ic in which
$R^1$ is H, $R^{1'}$ is chlorine, X is O and $R^3$ has one of the meanings given in table A.
Table 31:
Compounds of the formula Ic in which
$R^1$ is methyl, $R^{1'}$ is H, X is O and $R^3$ has one of the meanings given in table A.
Table 32:
Compounds of the formula Ic in which
$R^1$ is methyl, $R^{1'}$ is methyl, X is O and $R^3$ has one of the meanings given in table A.
Table 33:
Compounds of the formula Ic in which
$R^1$ is methyl, $R^{1'}$ is fluorine, X is O and $R^3$ has one of the meanings given in table A.
Table 34:
Compounds of the formula Ic in which
$R^1$ is methyl, $R^{1'}$ is chlorine, X is O and $R^3$ has one of the meanings given in table A.
Table 35:
Compounds of the formula Ic in which
$R^1$ is fluorine, $R^{1'}$ is H, X is O and $R^3$ has one of the meanings given in table A.
Table 36:
Compounds of the formula Ic in which
$R^1$ is fluorine, $R^{1'}$ is methyl, X is O and $R^3$ has one of the meanings given in table A.
Table 37:
Compounds of the formula Ic in which
$R^1$ is fluorine, $R^{1'}$ is fluorine, X is O and $R^3$ has one of the meanings given in table A.
Table 38:
Compounds of the formula Ic in which
$R^1$ is fluorine, $R^{1'}$ is chlorine, X is O and $R^3$ has one of the meanings given in table A.
Table 39:
Compounds of the formula Ic in which
$R^1$ is chlorine, $R^{1'}$ is H, X is O and $R^3$ has one of the meanings given in table A.
Table 40:
Compounds of the formula Ic in which
$R^1$ is chlorine, $R^{1'}$ is methyl, X is O and $R^3$ has one of the meanings given in table A.
Table 41:
Compounds of the formula Ic in which
$R^1$ is chlorine, $R^{1'}$ is fluorine, X is O and $R^3$ has one of the meanings given in table A.
Table 42:
Compounds of the formula Ic in which
$R^1$ is chlorine, $R^{1'}$ is chlorine, X is O and $R^3$ has one of the meanings given in table A.
Table 43:
Compounds of the formula IIc

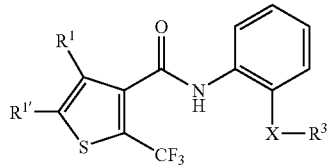

in which
$R^1$ is H, $R^{1'}$ is methyl, X is a direct bond and $R^3$ has one of the meanings given in table A.
Table 44:
Compounds of the formula IIc in which
$R^1$ is H, $R^{1'}$ is fluorine, X is a direct bond and $R^3$ has one of the meanings given in table A.
Table 45:
Compounds of the formula IIc in which
$R^1$ is H, $R^{1'}$ is chlorine, X is a direct bond and $R^3$ has one of the meanings given in table A.
Table 46:
Compounds of the formula IIc in which
$R^1$ is methyl, $R^{1'}$ is H, X is a direct bond and $R^3$ has one of the meanings given in table A.
Table 47:
Compounds of the formula IIc in which
$R^1$ is methyl, $R^{1'}$ is methyl, X is a direct bond and $R^3$ has one of the meanings given in table A.
Table 48:
Compounds of the formula IIc in which
$R^1$ is methyl, $R^{1'}$ is fluorine, X is a direct bond and $R^3$ has one of the meanings given in table A.
Table 49:
Compounds of the formula IIc in which
$R^1$ is methyl, $R^{1'}$ is chlorine, X is a direct bond and $R^3$ has one of the meanings given in table A.
Table 50:
Compounds of the formula IIc in which
$R^1$ is fluorine, $R^{1'}$ is H, X is a direct bond and $R^3$ has one of the meanings given in table A.
Table 51:
Compounds of the formula IIc in which
$R^1$ is fluorine, $R^{1'}$ is methyl, X is a direct bond and $R^3$ has one of the meanings given in table A.
Table 52:
Compounds of the formula IIc in which
$R^1$ is fluorine, $R^{1'}$ is fluorine, X is a direct bond and $R^3$ has one of the meanings given in table A.

Table 53:
Compounds of the formula IIc in which
$R^1$ is fluorine, $R^{1'}$ is chlorine, X is a direct bond and $R^3$ has one of the meanings given in table A.

Table 54:
Compounds of the formula IIc in which
$R^1$ is chlorine, $R^{1'}$ is H, X is a direct bond and $R^3$ has one of the meanings given in table A.

Table 55:
Compounds of the formula IIc in which
$R^1$ is chlorine, $R^{1'}$ is methyl, X is a direct bond and $R^3$ has one of the meanings given in table A.

Table 56:
Compounds of the formula IIc in which
$R^1$ is chlorine, $R^{1'}$ is fluorine, X is a direct bond and $R^3$ has one of the meanings given in table A.

Table 57:
Compounds of the formula IIc in which
$R^1$ is chlorine, $R^{1'}$ is chlorine, X is a direct bond and $R^3$ has one of the meanings given in table A.

Table 58:
Compounds of the formula IIc in which
$R^1$ is H, $R^{1'}$ is methyl, X is O and $R^3$ has one of the meanings given in table A.

Table 59:
Compounds of the formula IIc in which
$R^1$ is H, $R^{1'}$ is fluorine, X is O and $R^3$ has one of the meanings given in table A.

Table 60:
Compounds of the formula IIc in which
$R^1$ is H, $R^{1'}$ is chlorine, X is O and $R^3$ has one of the meanings given in table A.

Table 61:
Compounds of the formula IIc in which
$R^1$ is methyl, $R^{1'}$ is H, X is O and $R^3$ has one of the meanings given in table A.

Table 62:
Compounds of the formula IIc in which
$R^1$ is methyl, $R^{1'}$ is methyl, X is O and $R^3$ has one of the meanings given in table A.

Table 63:
Compounds of the formula IIc in which
$R^1$ is methyl, $R^{1'}$ is fluorine, X is O and $R^3$ has one of the meanings given in table A.

Table 64:
Compounds of the formula IIc in which
$R^1$ is methyl, $R^{1'}$ is chlorine, X is O and $R^3$ has one of the meanings given in table A.

Table 65:
Compounds of the formula IIc in which
$R^1$ is fluorine, $R^{1'}$ is H, X is O and $R^3$ has one of the meanings given in table A.

Table 66:
Compounds of the formula IIc in which
$R^1$ is fluorine, $R^{1'}$ is methyl, X is O and $R^3$ has one of the meanings given in table A.

Table 67:
Compounds of the formula IIc in which
$R^1$ is fluorine, $R^{1'}$ is fluorine, X is O and $R^3$ has one of the meanings given in table A.

Table 68:
Compounds of the formula IIc in which
$R^1$ is fluorine, $R^{1'}$ is chlorine, X is O and $R^3$ has one of the meanings given in table A.

Table 69:
Compounds of the formula IIc in which
$R^1$ is chlorine, $R^{1'}$ is H, X is O and $R^3$ has one of the meanings given in table A.

Table 70:
Compounds of the formula IIc in which
$R^1$ is chlorine, $R^{1'}$ is methyl, X is O and $R^3$ has one of the meanings given in table A.

Table 71:
Compounds of the formula IIc in which
$R^1$ is chlorine, $R^{1'}$ is fluorine, X is O and $R^3$ has one of the meanings given in table A.

Table 72:
Compounds of the formula IIc in which
$R^1$ is chlorine, $R^{1'}$ is chlorine, X is O and $R^3$ has one of the meanings given in table A.

Table 73:
Compounds of the formula IIIc

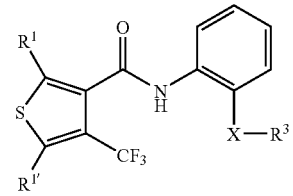

in which
$R^1$ is H, $R^{1'}$ is methyl, X is a direct bond and $R^3$ has one of the meanings given in table A.

Table 74:
Compounds of the formula IIIc in which
$R^1$ is H, $R^{1'}$ is fluorine, X is a direct bond and $R^3$ has one of the meanings given in table A.

Table 75:
Compounds of the formula IIIc in which
$R^1$ is H, $R^{1'}$ is chlorine, X is a direct bond and $R^3$ has one of the meanings given in table A.

Table 76:
Compounds of the formula IIIc in which
$R^1$ is methyl, $R^{1'}$ is H, X is a direct bond and $R^3$ has one of the meanings given in table A.

Table 77:
Compounds of the formula IIIc in which
$R^1$ is methyl, $R^{1'}$ is methyl, X is a direct bond and $R^3$ has one of the meanings given in table A.

Table 78:
Compounds of the formula IIIc in which
$R^1$ is methyl, $R^{1'}$ is fluorine, X is a direct bond and $R^3$ has one of the meanings given in table A.

Table 79:
Compounds of the formula IIIc in which
$R^1$ is methyl, $R^{1'}$ is chlorine, X is a direct bond and $R^3$ has one of the meanings given in table A.

Table 80:
Compounds of the formula IIIc in which
$R^1$ is fluorine, $R^{1'}$ is H, X is a direct bond and $R^3$ has one of the meanings given in table A.

Table 81:
Compounds of the formula IIIc in which
$R^1$ is fluorine, $R^{1'}$ is methyl, X is a direct bond and $R^3$ has one of the meanings given in table A.

Table 82:
Compounds of the formula IIIc in which
R$^1$ is fluorine, R$^{1'}$ is fluorine, X is a direct bond and R$^3$ has one of the meanings given in table A.

Table 83:
Compounds of the formula IIIc in which
R$^1$ is fluorine, R$^{1'}$ is chlorine, X is a direct bond and R$^3$ has one of the meanings given in table A.

Table 84:
Compounds of the formula IIIc in which
R$^1$ is chlorine, R$^{1'}$ is H, X is a direct bond and R$^3$ has one of the meanings given in table A.

Table 85:
Compounds of the formula IIIc in which
R$^1$ is chlorine, R$^{1'}$ is methyl, X is a direct bond and R$^3$ has one of the meanings given in table A.

Table 86:
Compounds of the formula IIIc in which
R$^1$ is chlorine, R$^{1'}$ is fluorine, X is a direct bond and R$^3$ has one of the meanings given in table A.

Table 87:
Compounds of the formula IIIc in which
R$^1$ is chlorine, R$^{1'}$ is chlorine, X is a direct bond and R$^3$ has one of the meanings given in table A.

Table 88:
Compounds of the formula IIIc in which
R$^1$ is H, R$^{1'}$ is methyl, X is O and R$^3$ has one of the meanings given in table A.

Table 89:
Compounds of the formula IIIc in which
R$^1$ is H, R$^{1'}$ is fluorine, X is O and R$^3$ has one of the meanings given in table A.

Table 90:
Compounds of the formula IIIc in which
R$^1$ is H, R$^{1'}$ is chlorine, X is O and R$^3$ has one of the meanings given in table A.

Table 91:
Compounds of the formula IIIc in which
R$^1$ is methyl, R$^{1'}$ is H, X is O and R$^3$ has one of the meanings given in table A.

Table 92:
Compounds of the formula IIIc in which
R$^1$ is methyl, R$^{1'}$ is methyl, X is O and R$^3$ has one of the meanings given in table A.

Table 93:
Compounds of the formula IIIc in which
R$^1$ is methyl, R$^{1'}$ is fluorine, X is O and R$^3$ has one of the meanings given in table A.

Table 94:
Compounds of the formula IIIc in which
R$^1$ is methyl, R$^{1'}$ is chlorine, X is O and R$^3$ has one of the meanings given in table A.

Table 95:
Compounds of the formula IIIc in which
R$^1$ is fluorine, R$^{1'}$ is H, X is O and R$^3$ has one of the meanings given in table A.

Table 96:
Compounds of the formula IIIc in which
R$^1$ is fluorine, R$^{1'}$ is methyl, X is O and R$^3$ has one of the meanings given in table A.

Table 97:
Compounds of the formula IIIc in which
R$^1$ is fluorine, R$^{1'}$ is fluorine, X is O and R$^3$ has one of the meanings given in table A.

Table 98:
Compounds of the formula IIIc in which
R$^1$ is fluorine, R$^{1'}$ is chlorine, X is O and R$^3$ has one of the meanings given in table A.

Table 99:
Compounds of the formula IIIc in which
R$^1$ is chlorine, R$^{1'}$ is H, X is O and R$^3$ has one of the meanings given in table A.

Table 100:
Compounds of the formula IIIc in which
R$^1$ is chlorine, R$^{1'}$ is methyl, X is O and R$^3$ has one of the meanings given in table A.

Table 101:
Compounds of the formula IIIc in which
R$^1$ is chlorine, R$^{1'}$ is fluorine, X is O and R$^3$ has one of the meanings given in table A.

Table 102:
Compounds of the formula IIIc in which
R$^1$ is chlorine, R$^{1'}$ is chlorine, X is O and R$^3$ has one of the meanings given in table A.

Table 103:
Compounds of the formula Id

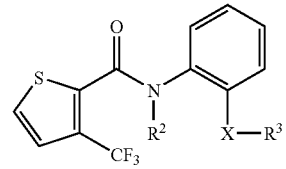

Id in which R$^2$ is methyl, X is a direct bond and R$^3$ has one of the meanings given in table A.

Table 104:
Compounds of the formula Id in which
R$^2$ is OH, X is a direct bond and R$^3$ has one of the meanings given-in table A.

Table 105:
Compounds of the formula Id in which
R$^2$ is methoxy, X is a direct bond and R$^3$ has one of the meanings given in table A.

Table 106:
Compounds of the formula Id in which
R$^2$ is methyl, X is O and R$^3$ has one of the meanings given in table A.

Table 107:
Compounds of the formula Id in which
R$^2$ is OH, X is O and R$^3$ has one of the meanings given in table A.

Table 108:
Compounds of the formula Id in which
R$^2$ is methoxy, X is O and R$^3$ has one of the meanings given in table A.

Table 109:

Compounds of the formula IId

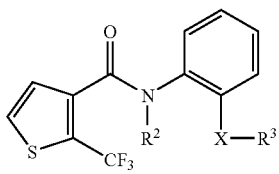

in which $R^2$ is methyl, X is a direct bond and $R^3$ has one of the meanings given in table A.

Table 110:

Compounds of the formula IId in which $R^2$ is OH, X is a direct bond and $R^3$ has one of the meanings given in table A.

Table 111:

Compounds of the formula IId in which $R^2$ is methoxy, X is a direct bond and $R^3$ has one of the meanings given in table A.

Table 112:

Compounds of the formula IId in which $R^2$ is methyl, X is O and $R^3$ has one of the meanings given in table A.

Table 113:

Compounds of the formula IId in which $R^2$ is OH, X is O and $R^3$ has one of the meanings given in table A.

Table 114:

Compounds of the formula IId in which $R^2$ is methoxy, X is O and $R^3$ has one of the meanings given in table A.

Table 115:

Compounds of the formula IIId

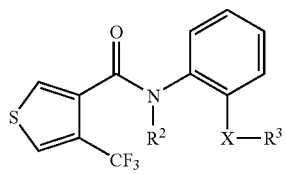

in which $R^2$ is methyl, X is a direct bond and $R^3$ has one of the meanings given in table A.

Table 116:

Compounds of the formula IIId in which $R^2$ is OH, X is a direct bond and $R^3$ has one of the meanings given in table A.

Table 117:

Compounds of the formula IIId in which $R^2$ is methoxy, X is a direct bond and $R^3$ has one of the meanings given in table A.

Table 118:

Compounds of the formula IIId in which $R^2$ is methyl, X is O and $R^3$ has one of the meanings given in table A.

Table 119:

Compounds of the formula IIId in which $R^2$ is OH, X is O and $R^3$ has one of the meanings given in table A.

Table 120:

Compounds of the formula IIId in which $R^2$ is methoxy, X is O and $R^3$ has one of the meanings given in table A.

General Synthesis

The active compounds I, II and III can be prepared by processes known from the literature by reacting activated trifluorothiophenecarboxylic acid derivatives IV with an aniline V [Houben-Weyl: "Methoden der organ. Chemie" [Methods of Organic Chemistry], Georg-Thieme-Verlag, Stuttgart, N.Y. 1985, Volume E5, pp. 941-1045.]. Activated carboxylic acid derivatives are, for example, halides, activated esters, anhydrides, azides, for example chlorides, fluorides, bromides, para-nitrophenyl esters, pentafluorophenyl esters, N-hydroxysuccinimides, hydroxybenzotriazol-1-yl esters.

a)

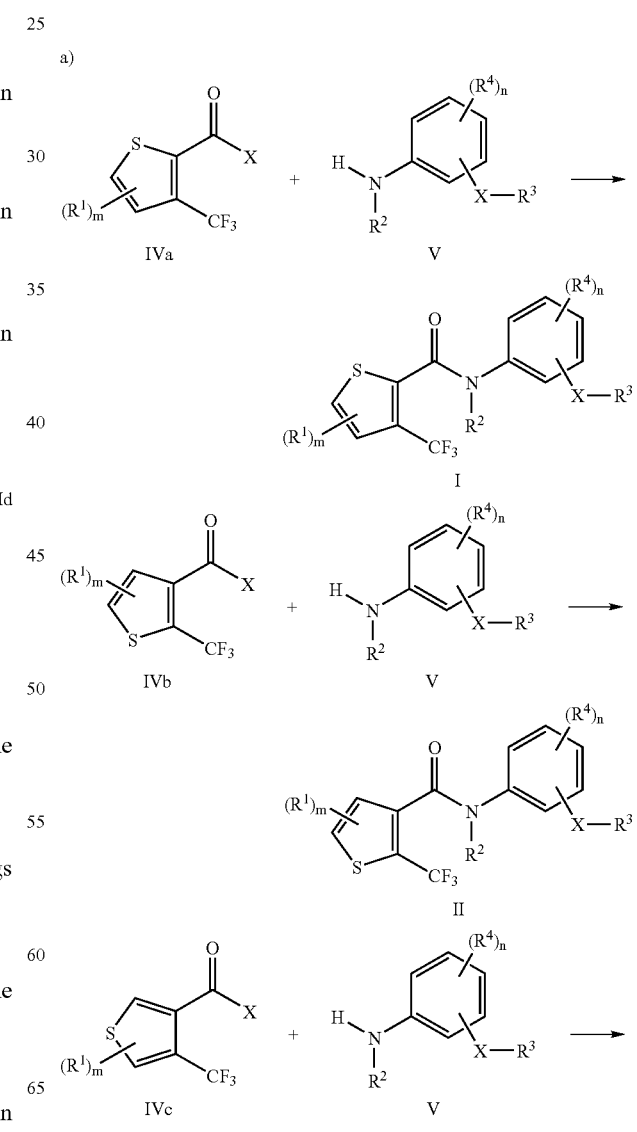

-continued

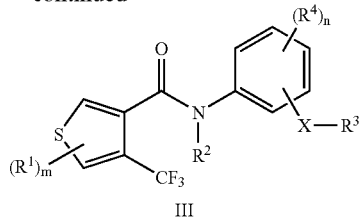

The active compounds I, II and III can be prepared by reacting the acids VI with an aniline V in the presence of a coupling agent.

b)

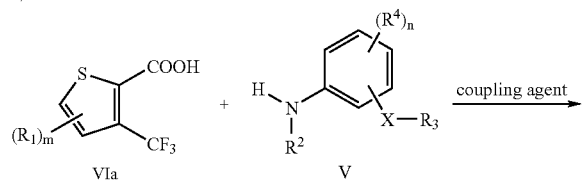

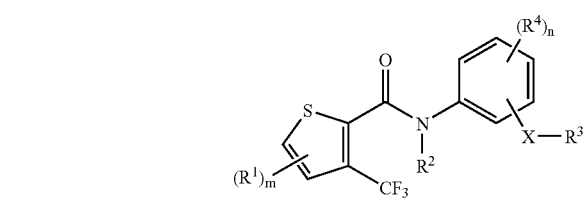

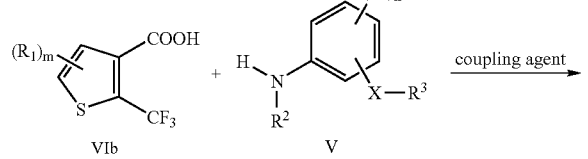

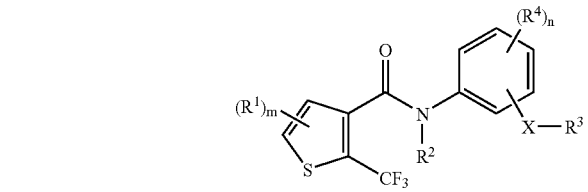

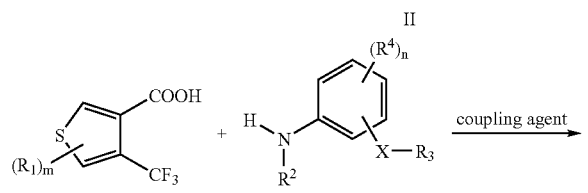

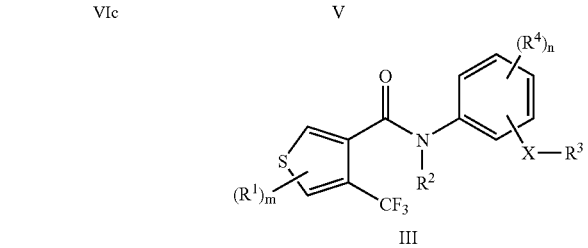

Suitable coupling agents are, for example:

coupling agents based on carbodiimides, for example N,N'-dicyclohexylcarbodiimide [J. C. Sheehan, G. P. Hess, J. Am. Chem. Soc. 1955, 77, 1067], N-(3-dimethylaminopropyl)-N'-ethylcarbodiimide;

coupling agents which form mixed anhydrides with carbonic esters, for example 2-ethoxy-1-ethoxycarbonyl-1,2-dihydroquinoline [B. Belleau, G. Malek, J. Amer. Chem. Soc. 1968, 90,1651.], 2-isobutyloxy-1-isobutyloxycarbonyl-1,2-dihydroquinoline [Y. Kiso, H. Yajima, J. Chem. Soc., Chem. Commun. 1972, 942.];

coupling agents composed of phosphonium base, for example (benzotriazol-1-yloxy)tris(dimethylamino) phosphonium hexafluorophosphate [B. Castro, J. R. Domoy, G. Evin, C. Selve, Tetrahedron Left. 1975, 14,1219.], (benzotriazol-1-yl-oxy)tripyrrolidinophosphonium hexafluorophosphate [J. Coste et al., Tetrahedron Lett. 1990, 31, 205.];

coupling agents based on uronium or having a guanidinium N-oxide structure, for example N,N,N',N'-tetramethyl-O-(1H-benzotriazol-1-yl)uronium hexafluorophosphate [R. Knorr, A. Trzeciak, W. Bannwarth, D. Gillessen, Tetrahedron Left. 1989, 30, 1927.], N,N,N',N'-tetramethyl-O-(benzotriazol-1-yl)uronium tetrafluoroborate, (benzotriazol-1-yloxy)dipiperidinocarbenium hexafluorophosphate [S. Chen, J. Xu, Tetrahedron Lett. 1992, 33, 647.];

coupling agents which form acid chlorides, for example bis(2-oxo-oxazolidinyl)phosphinic chloride [J. Diago-Mesequer, Synthesis 1980, 547.].

The active compounds I, II and III where $R^2$=unsubstituted or halogen-substituted alkyl or unsubstituted or halogen-substituted cycloalkyl can be prepared by alkylation of the amides I, II or III (in which $R^2$=hydrogen and which are obtainable by a) or b)) with suitable alkylating agents in the presence of bases:

c)

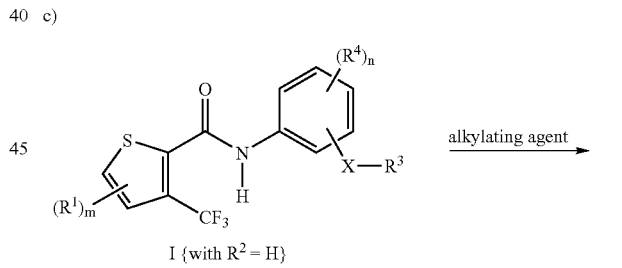

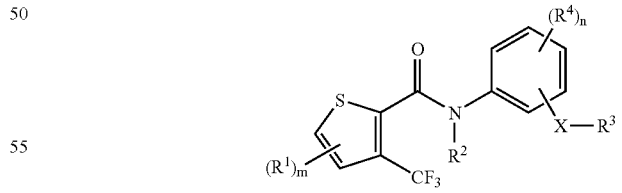

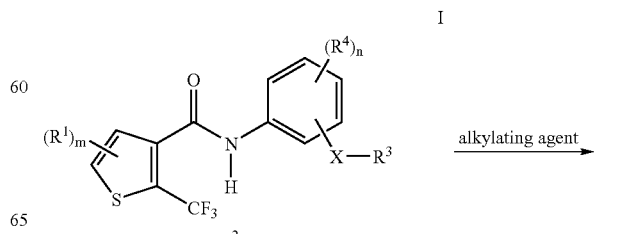

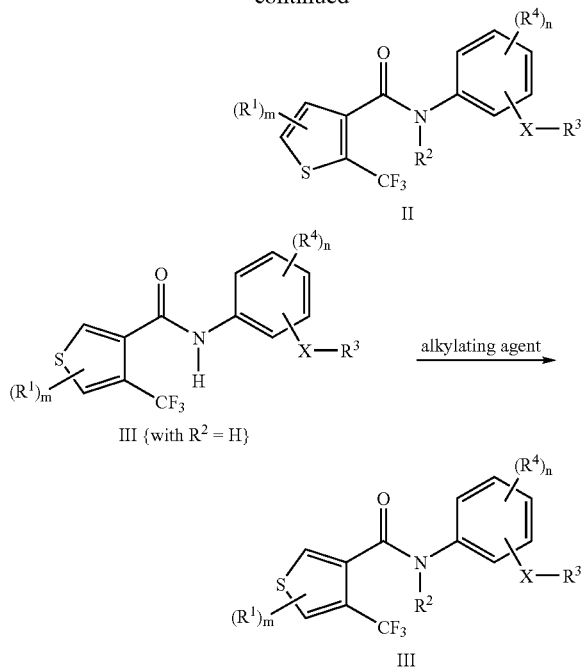

The trifluoromethylthiophenecarboxylic acids VI can be prepared by methods known from the literature [M. Nishida et al., J. Fluorine Chem. 1990, 46, 445. JP 1980-5059135. DE 3620064. U.S. Pat. No. 4,803,205. W. Dmowski, K. Piasecka, J. Fluorine Chem. 1996, 78, 59.]

Employing these, the activated thiophenecarboxylic acid derivatives IV can be synthesized by methods known from the literature [Houben-Weyl: "Methoden der organ. Chemie", Georg-Thieme-Verlag, Stuttgart, N.Y. 1985, Volume E5, pp. 587-614, 633-772.]

The anilines V can be synthesized by methods known from the literature [Houben-Weyl: "Methoden der organ. Chemie", Georg-Thieme-Verlag, Stuttgart, N.Y., Volume XI, Part 1, pp. 9-1005.]

The compounds I, II and III are suitable for use as fungicides. They are distinguished by an outstanding effectiveness against a broad spectrum of phytopathogenic fungi, especially from the classes of the *Ascomycetes, Deuteromycetes, Phycomycetes* and *Basidiomycetes*. Some are systemically effective and they can be used in plant protection as foliar and soil fungicides.

They are particularly important in the control of a multitude of fungi on various cultivated plants, such as wheat, rye, barley, oats, rice, maize, grass, bananas, cotton, soya, coffee, sugar cane, vines, fruits and ornamental plants, and vegetables, such as cucumbers, beans, tomatoes, potatoes and cucurbits, and on the seeds of these plants.

They are especially suitable for controlling the following plant diseases:

Alternaria species on fruit and vegetables,
*Botrytis cinerea* (gray mold) on strawberries, vegetables, ornamental plants and grapevines,
*Cercospora arachidicola* on groundnuts,
*Erysiphe cichoracearum* and *Sphaerotheca fuliginea* on cucurbits,
*Erysiphe graminis* (powdery mildew) on cereals,
*Fusarium* and *Verticillium* species on various plants,
*Helminthosporium* species on cereals,
*Mycosphaerella* species on bananas and groundnuts,
*Phytophthora infestans* on potatoes and tomatoes,
*Plasmopara viticola* on grapevines,
*Podosphaera leucotricha* on apples,
*Pseudocercosporella herpotrichoides* on wheat and barley,
*Pseudoperonospora* species on hops and cucumbers,
*Puccinia* species on cereals,
*Pyricularia oryzae* on rice,
*Rhizoctonia* species on cotton, rice and lawns,
*Septoria nodorum* on wheat,
*Sphaerotheca fuliginea* (mildew of cucumber) on cucumbers,
*Uncinula necator* on grapevines,
*Ustilago* species on cereals and sugar cane,
*Venturia* species (scab) on apples and pears,
*Septoria tritici*,
*Pyrenophora* species,
*Leptosphaeria nodorum*,
*Rhynchosporium* species and
*Typhula* species.

The compounds I, II and III are also suitable for controlling harmful fungi, such as *Paecilomyces varioti*, in the protection of materials (e.g. wood, paper, paint dispersions, fibers or fabrics) and in the protection of stored products.

The compounds I, II and III are employed by treating the fungi or the plants, seeds, materials or soil to be protected from fungal attack with a fungicidally effective amount of the active compounds. The application can be carried out both before and after the infection of the materials, plants or seeds by the fungi.

The fungicidal compositions generally comprise between 0.1 and 95%, preferably between 0.5 and 90%, by weight of active compound.

When employed in plant protection, the amounts applied are, depending on the kind of effect desired, between 0.01 and 2.0 kg of active compound per ha.

In seed treatment, amounts of active compound of 0.001 to 0.1 g, preferably 0.01 to 0.05 g, per kilogram of seed are generally necessary.

When used in the protection of materials or stored products, the amount of active compound applied depends on the kind of application area and on the effect desired. Amounts customarily applied in the protection of materials are, for example, 0.001 g to 2 kg, preferably 0.005 g to 1 kg, of active compound per cubic meter of treated material.

The compounds I, II and III can be converted to the usual formulations, e.g. solutions, emulsions, suspensions, dusts, powders, pastes and granules. The application form depends on the respective use intended; it should in any case guarantee a fine and uniform distribution of the compound according to the invention.

The formulations are prepared in a known way, e.g. by extending the active compound with solvents and/or carriers, if desired using emulsifiers and dispersants, it being possible, when water is the diluent, also to use other organic solvents as auxiliary solvents. Suitable auxiliaries for this purpose are essentially: solvents, such as aromatics (e.g. xylene), chlorinated aromatics (e.g. chlorobenzenes), paraffins (e.g. petroleum fractions), alcohols (e.g. methanol, butanol), ketones (e.g. cyclohexanone), amines (e.g. ethanolamine, dimethylformamide) and water; carriers, such as ground natural minerals (e.g. kaolins, clays, talc, chalk) and ground synthetic ores (e.g. highly dispersed silicic acid, silicates); emulsifiers, such as nonionic and anionic emulsifiers (e.g. polyoxyethylene fatty alcohol ethers, alkylsulfonates and arylsulfonates) and dispersants, such as lignosulfite waste liquors and methylcellulose.

Suitable surfactants are alkali metal, alkaline earth metal and ammonium salts of lignosulfonic acid, naphthalenesulfonic acid, phenolsulfonic acid and dibutylnaphthalenesulfonic acid, alkylarylsulfonates, alkyl sulfates, alkylsulfonates, fatty alcohol sulfates and fatty acids, and alkali metal and alkaline earth metal salts thereof, salts of sulfated fatty alcohol glycol ethers, condensation products of sulfonated naphthalene and naphthalene derivatives with formaldehyde, condensation products of naphthalene or of naphthalenesulfonic acid with phenol and formaldehyde, polyoxyethylene octylphenol ethers, ethoxylated isooctylphenol, octylphenol and nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignosulfite waste liquors and methylcellulose.

Petroleum fractions having medium to high boiling points, such as kerosene or diesel oil, furthermore coal tar oils, and oils of vegetable or animal origin, aliphatic, cyclic and aromatic hydrocarbons, e.g. benzene, toluene, xylene, paraffin, tetrahydronaphthalene, alkylated naphthalenes or derivatives thereof, methanol, ethanol, propanol, butanol, chloroform, carbon tetrachloride, cyclohexanol, cyclohexanone, chlorobenzene or isophorone, or highly polar solvents, e.g. dimethylformamide, dimethyl sulfoxide, N-methylpyrrolidone or water, are suitable for the preparation of directly sprayable solutions, emulsions, pastes or oil dispersions.

Powders, compositions for broadcasting and dusts can be prepared by mixing or mutually grinding the active substances with a solid carrier.

Granules, e.g. coated granules, impregnated granules and homogeneous granules, can be prepared by binding the active compounds to solid carriers. Solid carriers are, e.g., mineral earths, such as silica gels, silicic acids, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, such as, e.g., ammonium sulfate, ammonium phosphate, ammonium nitrate or ureas, and plant products, such as cereal meal, tree bark meal, wood meal and nutshell meal, cellulose powders and other solid carriers.

The formulations generally comprise between 0.01 and 95% by weight, preferably between 0.1 and 90% by weight, of the active compound. The active compounds are employed therein in a purity of 90% to 100%, preferably 95% to 100% (according to the NMR spectrum).

Examples for formulations are:

I. 5 parts by weight of a compound according to the invention are intimately mixed with 95 parts by weight of finely divided kaolin. In this way, a dust comprising 5% by weight of the active compound is obtained.

II. 30 parts by weight of a compound according to the invention are intimately mixed with a mixture of 92 parts by weight of pulverulent silica gel and 8 parts by weight of liquid paraffin, which had been sprayed onto the surface of this silica gel. In this way, an active compound preparation with good adhesive properties (active compound content 23% by weight) is obtained.

III. 10 parts by weight of a compound according to the invention are dissolved in a mixture consisting of 90 parts by weight of xylene, 6 parts by weight of the addition product of 8 to 10 mol of ethylene oxide with 1 mol of the N-monoethanolamide of oleic acid, 2 parts by weight of the calcium salt of dodecyl-benzenesulfonic acid and 2 parts by weight of the addition product of 40 mol of ethylene oxide with 1 mol of castor oil (active compound content 9% by weight).

IV. 20 parts by weight of a compound according to the invention are dissolved in a mixture consisting of 60 parts by weight of cyclohexanone, 30 parts by weight of isobutanol, 5 parts by weight of the addition product of 7 mol of ethylene oxide with 1 mol of isooctylphenol and 5 parts by weight of the addition product of 40 mol of ethylene oxide with 1 mol of castor oil (active compound content 16% by weight).

V. 80 parts by weight of a compound according to the invention are intimately mixed with 3 parts by weight of the sodium salt of diisobutylnaphthalene-alpha-sulfonic acid, 10 parts by weight of the sodium salt of a lignosulfonic acid from a sulfite waste liquor and 7 parts by weight of pulverulent silica gel and are ground in a hammer mill (active compound content 80% by weight).

VI. 90 parts by weight of a compound according to the invention are mixed with 10 parts by weight of N-methyl-a-pyrrolidone and a solution is obtained which is suitable for use in the form of very small drops (active compound content 90% by weight).

VII. 20 parts by weight of a compound according to the invention are dissolved in a mixture consisting of 40 parts by weight of cyclohexanone, 30 parts by weight of isobutanol, 20 parts by weight of the addition product of 7 mol of ethylene oxide with 1 mol of isooctylphenol and 10 parts by weight of the addition product of 40 mol of ethylene oxide with 1 mol of castor oil. By running the solution into 100 000 parts by weight of water and finely dispersing it therein, an aqueous dispersion is obtained comprising 0.02% by weight of the active compound.

VIII. 20 parts by weight of a compound according to the invention are intimately mixed with 3 parts by weight of the sodium salt of diisobutylnaphthalene-α-sulfonic acid, 17 parts by weight of the sodium salt of a lignosulfonic acid from a sulfite waste liquor and 60 parts by weight of pulverulent silica gel and are ground in a hammer mill. A spray emulsion comprising 0.1% by weight of the active compound is obtained by fine dispersion of the mixture in 20 000 parts by weight of water.

IX. 10 parts by weight of the compound according to the invention are dissolved in 63 parts by weight of cyclohexanone, 27 parts by weight of dispersing agent (for example a mixture of 50 parts by weight of the adduct of 7 mol of ethylene oxide to 1 mol of isooctylphenol and 50 parts by weight of the adduct of 40 mol of ethylene oxide to 1 mol of castor oil). The stock solution is then diluted to the desired concentration, for example a concentration in the range from 1 to 100 ppm, by distribution in water.

The active compounds can be used as such, in the form of their formulations or of the application forms prepared therefrom, e.g. in the form of directly sprayable solutions, powders, suspensions or dispersions, emulsions, oil dispersions, pastes, dusts, compositions for broadcasting or granules, by spraying, atomizing, dusting, broadcasting or watering. The application forms depend entirely on the intended uses; they should in any case guarantee the finest possible dispersion of the active compounds according to the invention.

Aqueous application forms can be prepared from emulsion concentrates, pastes or wettable powders (spray powders, oil dispersions) by addition of water. To prepare emulsions, pastes or oil dispersions, the substances can be homogenized in water, as such or dissolved in an oil or solvent, by means of wetting agents, tackifiers, dispersants or emulsifiers. However, concentrates comprising active substance, wetting agent, tackifier, dispersant or emulsifier and possibly solvent or oil can also be prepared, which concentrates are suitable for dilution with water.

The concentrations of active compound in the ready-to-use preparations can be varied within relatively wide ranges. In general, they are between 0.0001 and 10%. Often even small amounts of active compound I are sufficient in the ready-to-use preparation, for example 2 to 200 ppm. Ready-to-use preparations with concentrations of active compound in the range from 0.01 to 1% are also preferred.

The active compounds can also be used with great success in the ultra low volume (ULV) process, it being possible to apply formulations with more than 95% by weight of active compound or even the active compound without additives.

Oils of various types, herbicides, fungicides, other pesticides and bactericides can be added to the active compounds, if need be also not until immediately before use (tank mix). These agents can be added to the compositions according to the invention in a weight ratio of 1:10 to 10:1.

The compositions according to the invention can, in the application form as fungicides, also be present together with other active compounds, e.g. with herbicides, insecticides, growth regulators, fungicides or also with fertilizers. On mixing the compounds I or the compositions comprising them in the application form as fungicides with other fungicides, in many cases an expansion of the fungicidal spectrum of activity is obtained.

The following list of fungicides, with which the compounds according to the invention can be used in conjunction, is intended to illustrate the possible combinations but does not limit them:

sulfur, dithiocarbamates and their derivatives, such as iron (III) dimethyldithiocarbamate, zinc dimethyldithiocarbamate, zinc ethylenebisdithiocarbamate, manganese ethylenebisdithiocarbamate, manganese zinc ethylenediaminebisdithiocarbamate, tetramethylthiuram disulfide, ammonia complex of zinc (N,N-ethylenebisdithiocarbamate), ammonia complex of zinc (N,N'-propylenebisdithiocarbamate), zinc (N,N'-propylenebisdithiocarbamate) or N,N'-polypropylenebis(thiocarbamoyl)disulfide;

nitro derivatives, such as dinitro(1-methylheptyl)phenyl crotonate, 2-sec-butyl-4,6-dinitrophenyl 3,3-dimethylacrylate, 2-sec-butyl4,6-dinitrophenyl isopropyl carbonate or diisopropyl 5-nitroisophthalate;

heterocyclic substances, such as 2-heptadecyl-2-imidazoline acetate, 2,4-dichloro-6-(o-chloroanilino)-s-triazine, O,O-diethyl phthalimidophosphonothioate, 5-amino-1-[bis(dimethylamino)phosphinyl]-3-phenyl-1,2,4-triazole, 2,3-dicyano-1,4-dithioanthraquinone, 2-thio-1,3-dithiolo[4,5-b]quinoxaline, methyl 1-(butylcarbamoyl)-2-benzimidazolecarbamate, 2-(methoxycarbonylamino)benzimidazole, 2-(2-furyl)benzimidazole, 2-(4-thiazolyl)benzimidazole, N-(1,1,2,2-tetrachloroethylthio)tetrahydrophthalimide, N-(trichloromethylthio)tetrahydrophthalimide or N-(trichloromethylthio)phthalimide, N-dichlorofluoromethylthio-N',N'-dimethyl-N-phenylsulfamide, 5-ethoxy-3-trichloromethyl-1,2,3-thiadiazole, 2-thiocyanatomethylthiobenzothiazole, 1,4-dichloro-2,5-dimethoxybenzene, 4-(2-chlorophenylhydrazono)-3-methyl-5-isoxazolone, 2-thiopyridine 1-oxide, 8-hydroxyquinoline or its copper salt, 2,3-dihydro-5-carboxanilido-6-methyl-1,4-oxathiin, 2,3-dihydro-5-carboxanilido-6-methyl-1,4-oxathiin 4,4-dioxide, 2-methyl-5,6-dihydro-4H-pyran-3-carboxanilide, 2-methylfuran-3-carboxanilide, 2,5-dimethylfuran-3-carboxanilide, 2,4,5-trimethyl-furan-3-carboxanilide, N-cyclohexyl-2,5-dimethylfuran-3-carboxamide, N-cyclohexyl-N-methoxy-2,5-dimethylfuran-3-carboxamide, 2-methylbenzanilide, 2-iodobenzanilide, N-formyl-N-morpholine 2,2,2-trichloroethyl acetal, piperazine-1,4-diylbis-1-(2,2,2-trichloroethyl)formamide, 1-(3,4-dichloroanilino)-1-formyl-amino-2,2,2-trichloroethane, 2,6-dimethyl-N-tridecylmorpholine or its salts, 2,6-dimethyl-N-cyclododecylmorpholine or its salts, N-[3-(p-(tert-butyl)phenyl]-2-methylpropyl]-cis-2,6-dimethylmorpholine, N-[3-(p-(tert-butyl)phenyl)-2-methyl-propyl]piperidine, 1-[2-(2,4-dichlorophenyl)-4-ethyl-1,3-dioxolan-2-ylethyl]-1H-1,2,4-triazole, 1-[2-(2,4-dichlorophenyl)-4-(n-propyl)-1,3-dioxolan-2-ylethyl]-1H-1,2,4-triazole, N-(n-propyl)-N-(2,4,6-trichlorophenoxyethyl)-N'-imidazolylurea, 1-(4-chlorophenoxy)-3,3-dimethyl-1-(1H-1,2,4-triazol-1-yl)-2-butanone, 1-(4-chlorophenoxy)-3,3-dimethyl-1-(1H-1,2,4-triazol-1-yl)-2-butanol, (2RS,3RS)-1-[3-(2-chlorophenyl)-2-(4-fluorophenyl)oxiran-2-ylmethyl]-1H-1,2,4-triazole, a-(2-chlorophenyl)-a-(4-chlorophenyl)-5-pyrimidine methanol, 5-butyl-2-dimethylamino-4-hydroxy-6-methylpyrimidine, bis(p-chlorophenyl)-3-pyridinemethanol, 1,2-bis(3-ethoxycarbonyl-2-thioureido)benzene or 1,2-bis(3-methoxycarbonyl-2-thioureido)benzene, strobilurins, such as methyl E-methoxyimino[a-(o-tolyloxy)-o-tolyl]acetate, methyl E-2-{2-[6-(2-cyanophenoxy)pyrimidin-4-yloxy]phenyl}-3-methoxyacrylate, methyl E-methoxyimino[a-(2-phenoxyphenyl)]acetamide, methyl E-methoxyimino-[a-(2,5-dimethylphenoxy)-o-tolyl]acetamide, anilinopyrimidines, such as N-(4,6-dimethylpyrimidin-2-yl)aniline, N-[4-methyl-6-(1-propynyl)pyrimidin-2-yl]aniline or N-[4-methyl-6-cyclopropylpyrimidin-2-yl]-aniline, phenylpyrroles, such as 4-(2,2-difluoro-1,3-benzodioxol-4-yl)pyrrole-3-carbonitrile, cinnamamides, such as 3-(4-chlorophenyl)-3-(3,4-dimethoxyphenyl)acryloyl-morpholine, and various fungicides, such as dodecylguanidine acetate, 3-[3-(3,5-dimethyl-2-oxycyclohexyl)-2-hydroxyethyl] glutarimide, hexachlorobenzene, methyl N-(2,6-dimethylphenyl)-N-(2-furoyl)-DL-alaninate, N-(2,6-dimethylphenyl)-N-(2'-methoxyacetyl)-DL-alanine methyl ester, N-(2,6-dimethylphenyl)-N-chloroacetyl-D,L-2-aminobutyrolactone, N-(2,6-dimethylphenyl)-N-(phenylacetyl)-DL-alanine methyl ester, 5-methyl-5-vinyl-3-(3,5-dichlorophenyl)-2,4-dioxo-1,3-oxazolidine, 3-(3,5-dichlorophenyl)-5-methyl-5-methoxymethyl-1, 3-oxazolidine-2,4-dione, 3-(3,5-dichlorophenyl)-1-isopropylcarbamoylhydantoin, N-(3,5-dichlorophenyl)-1,2-dimethylcyclopropane-1,2-dicarboximide, 2-cyano-N-(ethylaminocarbonyl)-2-[methoxyimino]acetamide, 1-[2-(2,4-dichlorophenyl)pentyl]-1H-1,2,4-triazole, 2,4-difluoro-a-(1H-1,2,4-triazolyl-1-methyl)benzhydryl alcohol, N-(3-chloro-2,6-dinitro-4-trifluoromethylphenyl)-5-trifluoromethyl-3-chloro-2-aminopyridine, 1-((bis(4-fluorophenyl)methylsilyl)methyl)-1H-1,2,4-triazole.

Preparation Examples:

a) Synthesis of N-(3-isopropoxyphenyl)-2-trifluoromethylthiophene-3-carboxamide: 12.9 g of 2-trifluoromethylthiophene-3-carboxylic acid are dissolved in 78 g of thionyl chloride, and the reaction mixture is heated under reflux for 2 h. The mixture is then concentrated under reduced pressure, giving 13.5 g of 2-trifluoromethylthiophene-3-carbonyl chloride. 1.0 g of this is added dropwise to a solution of 0.7 g of meta-isopropoxyaniline and 1.4 g of triethylamine in 35 ml of dichloromethane. The mixture is stirred at room temperature for 15 h. The mixture is then washed once with in each case 20 ml of 2% strength hydrochloric acid and saturated NaHCO₃ solution, and the organic phase is dried over magnesium sulfate and concentrated under reduced pressure. Chromatographic purification using a mixture of methyl tert-butyl ether and cyclohexane gives 1.15 g of the product. M.p.=58-60° C.

b) Synthesis of N-(2-(2,2,2-trifluoroethoxy)phenyl)-3-trifluoromethylthiophene-2-carboxamide:

0.39 g of 3-trifluoromethylthiophene-2-carboxylic acid, 0.36 g of 2-(2,2,2-trifluoroethoxy)aniline, 0.53 g of bis(2-oxo-3-oxazolidinyl)phosphinic chloride and 0.29 g of triethylamine are dissolved in 20 ml of dichloromethane. The mixture is stirred at room temperature for 15 h. 60 ml of methyl tert-butyl ether are then added, the mixture is washed in each case once with 5% strength hydrochloric acid, 5% strength aqueous sodium hydroxide solution and water and the organic phase is dried with magnesium sulfate and concentrated under reduced pressure. Chromatographic purification using a mixture of methyl tert-butyl ether and toluene gives 0.56 g of the product. M.p.=125-127° C.

c) Synthesis of N-(3-isopropoxyphenyl)-3-trifluoromethylthiophene-4-carboxamide: 0.30 g of 3-trifluoromethylthiophene-4-carboxylic acid, 0.23 g of 3-isopropyloxyaniline and 0.31 g of triethylamine and 0.43 g of bis(2-oxo-3-oxazolidinyl)-phosphinic chloride are dissolved in 30 ml of dichloromethane at 0° C. The mixture is stirred at 0° C. for 15 h and then at room temperature for 7 h. 60 ml of methyl tert-butyl ether are then added, the mixture is washed in each case once with 5% strength hydrochloric acid, 5% strength sodium bicarbonate solution and water and the organic phase is dried over magnesium sulfate and concentrated under reduced pressure. Chromatographic purification using a mixture of methyl tert-butyl ether and toluene gives 0.4 g of the product as an oil.

The compounds listed in tables 121, 122 and 123 are prepared analogously to the synthesis examples described above.

a) 3-Trifluoromethylthiophene-2-carboxanilides

TABLE 121

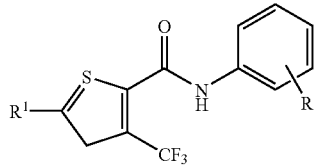

I

| No. | R | Pos. R | R¹ | m.p./consistency | Spectroscopic data |
|---|---|---|---|---|---|
| I-1 | ortho | sec-butyl | H | 69-70° C. | |
| I-2 | ortho | cyclopentyl | H | 139-141° C. | |
| I-3 | ortho | cyclohexyl | H | 100-101° C. | |
| I-4 | ortho | n-pentyl | H | 88-89° C. | |
| I-5 | ortho | 1,1,2,2-tetrafluoroethoxy | H | 59-61° C. | |
| I-6 | ortho | para-chlorophenyl | H | 148-150° C. | |
| I-7 | ortho | para-fluorophenyl | H | 121-122° C. | |
| I-8 | meta | isopropyloxy | H | 58-60° C. | |
| I-9 | meta | 1,1,2,2-tetrafluoroethoxy | H | resin | IR[cm⁻¹]: 1659, 1609, 1552, 1491, 1443, 1397, 1292, 1252, 1197, 1126, 909, 797, 768, 725, 680. |
| I-10 | meta | n-hexyloxy | H | 73-74° C. | |
| I-11 | meta | cyclopentyloxy | H | resin | IR[cm⁻¹]: 2961, 1657, 1610, 1599, 1553, 1491, 1442, 1396, 1290, 1257, 1156, 1130, 908, 770, 725. |
| I-12 | ortho | phenyl | H | 113-115° C. | |
| I-13 | ortho | para-isopropylphenyl | H | 125-126° C. | |
| I-14 | ortho | 2,2,2-trifluoroethoxy | H | 125-127° C. | |
| I-15 | ortho | 2,2,3,3,3-pentafluoropropyloxy | H | 56-58° C. | |
| I-16 | ortho | 2,2,3,3,4,4,5,5,6,6,7,7,7-tridecafluoroheptyloxy | H | | IR[cm⁻¹]: 1687, 1608, 1545, 1526, 1454, 1293, 1241, 1207, 1145, 1128, 748. |
| I-17 | ortho | sec-butyl | methyl | resin | 7.75(m, 1H); 7.67 (s(broad), 1H): 7.18-7.29 (m, 4H); 6.99(s; 1H); 2.76-2.85(m, 1H); 2.53(s, 3H); 1.51-1.69(m, 2H); 1.24(d, 3H); 0.86(t, 3H). |

TABLE 121-continued

I

[Structure: thiophene ring with R¹ at 5-position, CF₃ at 3-position, and C(=O)NH-phenyl-R at 2-position]

| No. | R | Pos. R | R¹ | m.p./consistency | Spectroscopic data |
|---|---|---|---|---|---|
| I-18 | ortho | para-chlorophenyl | methyl | 69-72° C. | |
| I-19 | meta | isopropyloxy | methyl | 93-96° C. | |
| I-20 | ortho | 1,1,2,2-tetrafluoroethoxy | methyl | 59-62° C. | |

Pos. R = position of R substituent relative to N—H group
m.p. = melting point b) 2-Trifluoromethylthiophene-3-carboxanilides

TABLE 122

II

[Structure: thiophene with CF₃ at 2-position and C(=O)NH-phenyl-R at 3-position]

| No. | Pos. R | R | m.p./consistency | Spectroscopic data |
|---|---|---|---|---|
| II-1 | ortho | sec-butyl | 92-93° C. | |
| II-2 | ortho | cyclopentyl | 161-163° C. | |
| II-3 | ortho | cyclohexyl | 101-103° C. | |
| II-4 | ortho | n-pentyl | 100-102° C. | |
| II-5 | ortho | 1,1,2,2-tetrafluoroethoxy | 78-79° C. | |
| II-6 | ortho | para-chlorophenyl | 152-153° C. | |
| II-7 | ortho | para-fluorophenyl | 99-101° C. | |

TABLE 122-continued

II

| No. | Pos. R | R | m.p./consistency | Spectroscopic data |
|---|---|---|---|---|
| II-8 | meta | isopropyloxy | resin | IR[cm$^{-1}$]: 2978, 1659, 1611, 1599, 1555, 1492, 1431, 1296, 1259, 1201, 1133, 1021, 1005, 688. |
| II-9 | meta | 1,1,2,2-tetrafluoroethoxy | resin | IR[cm$^{-1}$]: 1662, 1609, 1555, 1491, 1432, 1298, 1254, 1195, 1130, 1022, 852, 796, 760, 721, 684. |
| II-10 | meta | n-hexyloxy | resin | IR[cm$^{-1}$]: 2955, 2932, 1659, 1611, 1600, 1555, 1494, 1469, 1432, 1295, 1259, 1200, 1178, 1133, 1021. |

Pos. R = position of R substituent relative to N—H group
m.p. = melting point c) 3-Trifluoromethylthiophene-4-carboxanilides

TABLE 123

III

[Structure: thiophene with CF₃ at 4-position and C(=O)NH-phenyl-R at 3-position]

| No. | Pos. R | R | m.p./consistency | Spectroscopic data |
|---|---|---|---|---|
| III-1 | ortho | para-chlorophenyl | 130-134° C. | |
| III-2 | meta | isopropyloxy | oil | 1H NMR(CDCl₃), δ [ppm]: 1.30(d, 6H); 4.53(q, 1H); 6.70(m, 1H); 7.05 |

TABLE 123-continued

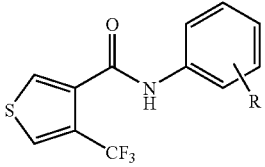

| No. | Pos. R | R | m.p./consistency | Spectroscopic data |
|---|---|---|---|---|
| | | | | (m, 1H); 7.25(m, 1H); 7.30(m, 1H); 7.70(s, 1H); 7.80(m, 1H); 7.88(m, 1H). |
| III-3 | ortho | para-fluorophenyl | 120-122° .C | |
| III-4 | ortho | ortho-methylphenyl | 86-87° C. | |
| III-5 | ortho | sec-butyl | 99-100° C. | |
| III-6 | ortho | n-pentyl | 106-108° C. | |
| III-7 | ortho | cyclopentyl | 110-113° C. | |
| III-8 | ortho | cyclohexyl | 142-143° C. | |
| III-9 | ortho | 1,1,2,2-tetrafluoroethoxy | 85°87° C. | |
| III-10 | ortho | 2,2,3,3-tetrafluoropropyloxy | 81-82° C. | |
| III-11 | ortho | 2,2,3,3,3-pentafluoropropyloxy | 90-92° C. | |
| III-12 | meta | cyclopentyloxy | 82-84° C. | |
| III-13 | meta | 1,1,2,2-tetrafluoroethoxy | 78-83° C. | |
| III-14 | ortho | phenyl | 82-85° C. | |
| III-15 | ortho | 2,2,3-trifluoroethoxy | 93-97° C. | |
| III-16 | ortho | para-(isopropyl)-phenyl | 79-83° C. | |

Pos. R = position of R substituent relative to N—H group
m.p. = melting point

USE EXAMPLE 1

Activity and Persistency against Gray Mold, Caused by *Botrytis cinerea*, on Bell-pepper Leaves Bell-pepper seedlings of the cultivar "Neusiedler Ideal Elite" having 4-5 well-developed leaves were sprayed to run-off point with an aqueous suspension having the concentration stated below of active compounds. The suspension or emulsion was prepared from a stock solution containing 10% of active compound in a mixture comprising 85% of cyclohexanone and 5% of emulsifier. The plants were then cultivated for a further 7 days, and the treated plants were then inoculated with a spore suspension of *Botrytis cinerea*, which comprised $1.7 \times 10^6$ spores/ml in a 2% strength aqueous biomalt solution. The test plants were then placed in a climatized chamber at 22-24° C. in high atmospheric humidity. After 5 days, the extent of the fungal infection on the leaves could be determined visually in %, giving not only an indication of the fungicidal action of the substances but also of the persistency.

| Number | Foliar infection [%] at 63 ppm |
|---|---|
| I-1 | 5 |
| I-2 | 7 |
| I-3 | 3 |
| I-5 | 3 |
| I-6 | 1 |
| I-7 | 1 |
| I-8 | 10 |
| I-11 | 7 |
| II-2 | 10 |
| II-3 | 5 |
| II-5 | 3 |
| II-7 | 1 |
| II-8 | 5 |
| II-10 | 10 |
| Untreated | 90 |

USE EXAMPLE 2

Protective Activity against Gray Mold, Caused by *Botrytis cinerea*, on Bell-pepper Leaves Bell-pepper seedlings of the cultivar "Neusiedler Ideal Elite" having 4-5 well-developed leaves were sprayed to run-off point with an aqueous suspension having the concentration stated below of active compounds. The active compounds were separately prepared as a stock solution containing 0.25% by weight of active compound in acetone or dimethyl sulfoxide. This solution was admixed with 1% by weight of Emulgator Uniperol® EL (wetting agent based on ethoxylated alkylphenols which has an emulsifying and dispersing effect) and diluted with water to the desired concentration. The next day, the treated plants were inoculated with a spore suspension of *Botrytis cinerea*, comprising $1.7 \times 10^6$ spores/ml in a 2% strength aqueous biomalt solution. The test plants were then placed in a climatized chamber at 22-24° C.

in high atmospheric humidity. After 5 days, the extent of the fungal infection on the leaves could be determined visually in %.

| Number | Foliar infection [%] at 250 ppm |
|---|---|
| III-4 | 3 |
| III-5 | 3 |
| III-7 | 7 |
| Untreated | 100 |

USE EXAMPLE 3

Protective Activity Against Mildew of Cucumber Caused by *Sphaerotheca fuliginea*

Leaves of potted cucumber seedlings of the cultivar "Chinese Snake", in the cotyledon stage, were sprayed to runoff point with an aqueous suspension having the concentration stated below of active compounds. The suspension or emulsion was prepared from a stock solution containing 10% of active compound in a mixture comprising 85% of cyclohexanone and 5% of emulsifier. 20 hours after the spray coating had dried on, the plants were inoculated with an aqueous spore suspension of mildew of cucumber (*Sphaerotheca fuliginea*). The plants were then cultivated in a greenhouse at 20-24° C. and 60-80% relative atmospheric humidity for 7 days. The extent of mildew development was then determined visually in % infection of the cotyledon area.

| Number | Foliar infection [%] at 63 ppm |
|---|---|
| I-3 | 5 |
| I-5 | 5 |
| I-6 | 0 |
| I-7 | 0 |
| I-12 | 0 |
| I-13 | 0 |
| II-3 | 3 |
| II-6 | 0 |
| II-7 | 5 |
| Untreated | 90 |

We claim:
1. A trifluoromethylthiophenecarboxanilide of the formulae I, II and III

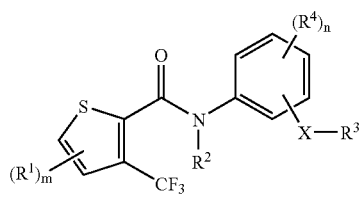

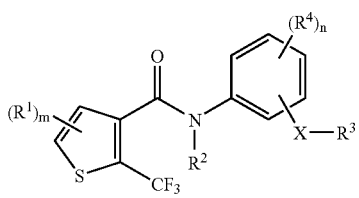

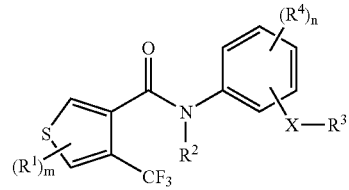

in which the substituents are as defined below:
$R^1$, $R^4$ independently of one another are $C_1$-$C_4$-alkyl, $C_3$-$C_6$-cycloalkyl, $C_2$-$C_4$-alkenyl, $C_2$-$C_4$-alkynyl, $C_1$-$C_4$-alkoxy (it being possible for these groups to be substituted by halogen), H, halogen, nitro, CN;

$R^2$ is $C_1$-$C_4$-alkyl, $C_3$-$C_6$-cycloalkyl, $C_1$-$C_4$-alkoxy (it being possible for these groups to be substituted by halogen), H, OH;

$R^3$ is $C_1$-$C_{12}$-alkyl, $C_3$-$C_{12}$-cycloalkyl, $C_2$-$C_{12}$-alkenyl, $C_5$-$C_{12}$-cycloalkenyl, $C_2$-$C_{12}$-alkynyl, $C_3$-$C_{12}$-cycloalkyl-$C_1$-$C_4$-alkyl (it being possible for these groups to be substituted by $R^7$);

phenyl, phenyl-$C_1$-$C_6$-alkyl, phenyl-$C_2$-$C_6$-alkenyl, phenyl-$C_2$-$C_6$-alkynyl, phenyloxy-$C_1$-$C_6$-alkyl, phenyloxy-$C_2$-$C_6$-alkenyl, phenyloxy-$C_2$-$C_6$-alkynyl, where the alkyl, alkenyl and alkynyl moiety may be substituted by $R^7$ and the phenyl ring may be substituted by $R^5$;

—$C(R^8)$=$NOR^6$;

X is O, S or a direct bond;

$R^5$ is H, $C_1$-$C_4$-alkyl, $C_3$-$C_6$-cycloalkyl, $C_1$-$C_4$-alkoxy, $C_2$-$C_4$-alkenyl, $C_2$-$C_4$-alkynyl (it being possible for these groups to be substituted by halogen), halogen, nitro, CN, phenyl (which may be substituted by $R^1$), phenoxy (which may be substituted by $R^1$), $C_1$-$C_6$-alkylphenyl, where the alkyl moiety may be substituted by halogen and the phenyl ring may be substituted by $R^1$;

$R^6$ is $C_1$-$C_4$-alkyl, $C_3$-$C_6$-cycloalkyl, $C_2$-$C_4$-alkenyl, $C_2$-$C_4$-alkynyl (it being possible for these groups to be substituted by halogen), phenyl, which may be substituted by $R^1$;

$R^7$ is $C_1$-$C_4$-alkyl, $C_1$-$C_8$-alkoxy, $C_2$-$C_8$-alkenyloxy, $C_2$-$C_8$-alkynyloxy, $C_1$-$C_4$-alkoxy-$C_1$-$C_8$-alkoxy (it being possible for these groups to be substituted by halogen), halogen;

$R^8$ is H, $R^7$ or $C_1$-$C_{12}$-alkyl, $C_3$-$C_{12}$-cycloalkyl, $C_2$-$C_{12}$-alkenyl, $C_5$-$C_{12}$-cycloalkenyl, $C_3$-$C_{12}$-cycloalkyl-$C_1$-$C_4$-alkyl (it being possible for these groups to be substituted by halogen);

phenyl, which may be substituted by $R^5$;

n is 0-4;
m is 0, 1.

2. A trifluoromethylthiophenecarboxanilide of the formula I, II or III according to claim 1 in which
$R^1$ is H, halogen or $C_1$-$C_4$alkyl, which may be substituted by halogen.

3. A trifluoromethylthiophenecarboxanilide of the formula I, II or III according to claim 2 in which
$R^1$ is fluorine, chlorine, bromine or methyl.

4. A trifluoromethylthiophenecarboxanilide of the formula I, II or III according to any of claims 1 to 3 in which
$R^2$ is H, methyl, OH or methoxy.

5. A trifluoromethylthiophenecarboxanilide of the formula I, II or III according to claim 1 in which $R^3$ is $C_1$-$C_{12}$-alkyl, $C_3$-$C_{12}$-cycloalkyl, $C_2$-$C_{12}$-alkenyl, $C_5$-$C_{12}$-cycloalkenyl, $C_2$-$C_{12}$-alkynyl, it being possible for these groups to be substituted by halogen and $C_1$-$C_4$-alkyl; phenyl, phenyl-$C_1$-$C_6$-alkyl, it being possible for the phenyl ring to be substituted by $R^5$; or —C($C_1$-$C_4$-alkyl)=NO—$R^6$, it being possible for the $C_1$-$C_4$-alkyl group to be substituted by halogen.

6. A trifluoromethylthiophenecarboxanilide of the formula I, II or III according to claim 1 in which $R^4$ is $C_1$-$C_4$-alkyl, $C_1$-$C_4$-alkoxy (it being possible for these groups to be substituted by halogen) or halogen.

7. A trifluoromethylthiophenecarboxanilide of the formula I, II or III according to claim 1 in which X is a direct bond or O.

8. A trifluoromethylthiophenecarboxanilide of the formulae Ia, Ib, IIa, IIb, IIIa and IIIb according to claim 1

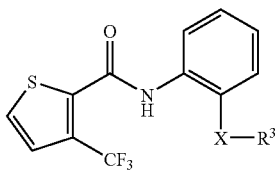
Ia

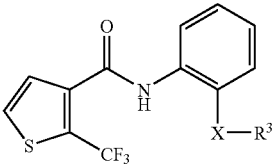
IIa

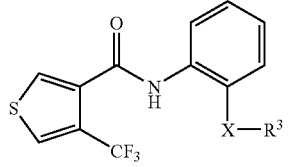
IIIa

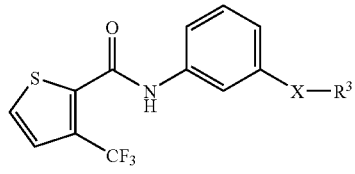
Ib

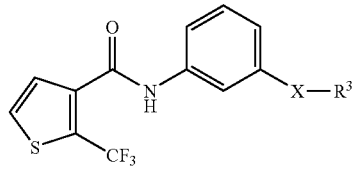
IIb

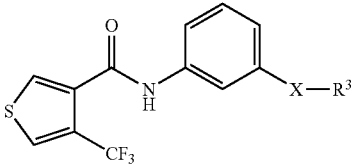
IIIb in which the substituents are as defined below:

$R^3$ is $C_1$-$C_{12}$-alkyl, $C_3$-$C_{12}$-cycloalkyl, $C_2$-$C_{12}$-alkenyl, $C_5$-$C_{12}$-cycloalkenyl, $C_2$-$C_{12}$-alkynyl,
 it being possible for these groups to be substituted by halogen or $C_1$-$C_4$-alkyl;
phenyl, phenyl-$C_1$-$C_6$-alkyl, it being possible for the phenyl ring to be substituted by $R^5$, or
—C($C_1$-$C_4$-alkyl)=NO—$R^6$, it being possible for the $C_1$-$C_4$-alkyl group to be substituted by halogen;

X is a direct bond or O.

9. A trifluoromethylthiophenecarboxanilide of the formulae Ia, Ib, IIa, IIb, IIIa and IIIb according to claim 8 in which X is a direct bond.

10. A trifluoromethylthiophenecarboxanilide of the formulae Ia, Ib, IIa, IIb, IIIa and IIIb according to claim 8 in which X is oxygen.

11. A method of controlling harmful fungi, wherein the harmful fungi, their habitat or the plants, areas, materials or spaces to be kept free from them are treated with the trifluoromethylthiophenecarboxanilides of the formula Ia, Ib, IIa, IIb, IIIa or IIIb according to claim 8.

12. A fungicidal composition comprising a fungicidally effective amount of at least one trifluoromethylthiophenecarboxanilide of the formula I, II or III according to claim 1.

13. A method of controlling harmful fungi, wherein the harmful fungi, their habitat or the plants, areas, materials or spaces to be kept free from them are treated with a fungicidal composition according to claim 12 comprising at least a fungicidally effective amount of a trifluoromethylthiophenecarboxanilide of the formula I, II or III.

* * * * *